United States Patent
Fujita et al.

(10) Patent No.: US 9,258,474 B2
(45) Date of Patent: Feb. 9, 2016

(54) IMAGE CAPTURING APPARATUS, COMPONENT MOUNTING APPARATUS, COMPONENT TESTING APPARATUS, AND SUBSTRATE INSPECTION APPARATUS

(75) Inventors: Haruyasu Fujita, Iwata (JP); Mamoru Suzuki, Iwata (JP)

(73) Assignee: Yamaha Hatsudoki Kabushiki Kaisha, Shizuoka-ken (JP)

( * ) Notice: Subject to any disclaimer, the term of this patent is extended or adjusted under 35 U.S.C. 154(b) by 5 days.

(21) Appl. No.: 14/236,833

(22) PCT Filed: Mar. 1, 2012

(86) PCT No.: PCT/JP2012/001419
§ 371 (c)(1),
(2), (4) Date: Feb. 3, 2014

(87) PCT Pub. No.: WO2013/018247
PCT Pub. Date: Feb. 7, 2013

(65) Prior Publication Data
US 2014/0184847 A1    Jul. 3, 2014

(30) Foreign Application Priority Data
Aug. 3, 2011 (JP) ................. 2011-169959

(51) Int. Cl.
*H04N 5/232* (2006.01)
*H04N 5/235* (2006.01)
(Continued)

(52) U.S. Cl.
CPC ............. *H04N 5/232* (2013.01); *H04N 5/2354* (2013.01); *H04N 5/37206* (2013.01); *G01N 2021/95638* (2013.01)

(58) Field of Classification Search
CPC . H04N 5/37206; H04N 5/372; H04N 5/3743; H04N 3/1525; H04N 5/232; H04N 5/2354; G01N 2021/95638
USPC ......... 348/68, 69, 70, 92, 105, 106, 125, 126, 348/131, 132, 142, 221.1, 222.1, 229.1, 348/230.1, 267, 268, 269, 270, 271, 272, 348/281, 282, 283, 294, 295, 296, 302, 303, 348/304, 311, 312, 316, 319, 320, 321, 322, 348/323, 324
See application file for complete search history.

(56) References Cited

U.S. PATENT DOCUMENTS

| | | | | |
|---|---|---|---|---|
| 4,800,258 A | * | 1/1989 | Suzuki | G06K 7/084 235/475 |
| 5,101,266 A | * | 3/1992 | Schlig | H04N 9/045 348/271 |

(Continued)

FOREIGN PATENT DOCUMENTS

| | | |
|---|---|---|
| JP | 07-087263 A | 3/1995 |
| JP | 08-251407 A | 9/1996 |

(Continued)

OTHER PUBLICATIONS

The extended European search report issued by the European Patent Office on Dec. 3, 2014, which corresponds to European Patent Application No. 12819581.5-1902 and is related to U.S. Appl. No. 14/263,833.

(Continued)

*Primary Examiner* — Twyler Haskins
*Assistant Examiner* — Peter Chon
(74) *Attorney, Agent, or Firm* — Studebaker & Brackett PC

(57) ABSTRACT

The TDI sensor includes: a light receiving unit including pixel rows each having a plurality of image capturing elements arranged in a first direction and generating and holding electric charges corresponding to respective exposure amounts, and electric charge holding rows each having a plurality of electric charge holding sections having only a function of holding the electric charges and arranged in the first direction so as to correspond to respective image capturing elements of the pixel rows, one of the pixel rows and one or a plurality of the electric charge holding rows being alternately arranged in a second direction orthogonal to the first direction; and a transfer unit that sequentially, on a row-by-row basis, transfers electric charges held by the image capturing elements and the electric charge holding sections to adjacent rows, and outputs a signal corresponding to electric charges finally accumulated by the transfer.

12 Claims, 13 Drawing Sheets

(51) Int. Cl.
*H04N 5/372* (2011.01)
*G01N 21/956* (2006.01)

(56) References Cited

U.S. PATENT DOCUMENTS

| | | | | |
|---|---|---|---|---|
| 5,917,620 | A * | 6/1999 | Hasegawa | H04N 1/401 348/262 |
| 7,009,163 | B2 * | 3/2006 | Katzir | G01N 21/8851 250/208.1 |
| 2002/0113196 | A1 * | 8/2002 | Hou | H04N 5/37206 250/208.1 |
| 2003/0006364 | A1 | 1/2003 | Katzir et al. | |
| 2003/0202095 | A1 * | 10/2003 | Schultz | H04N 1/00795 348/142 |
| 2010/0208116 | A1 | 8/2010 | Iijima | |

FOREIGN PATENT DOCUMENTS

| | | |
|---|---|---|
| JP | 2002-277406 A | 9/2002 |
| JP | 2005-107716 A | 4/2005 |
| JP | 2008-275611 A | 11/2008 |
| JP | 2009-170517 A | 7/2009 |

OTHER PUBLICATIONS

International Search Report; PCT/JP2012/001419; Jun. 5, 2012.

* cited by examiner

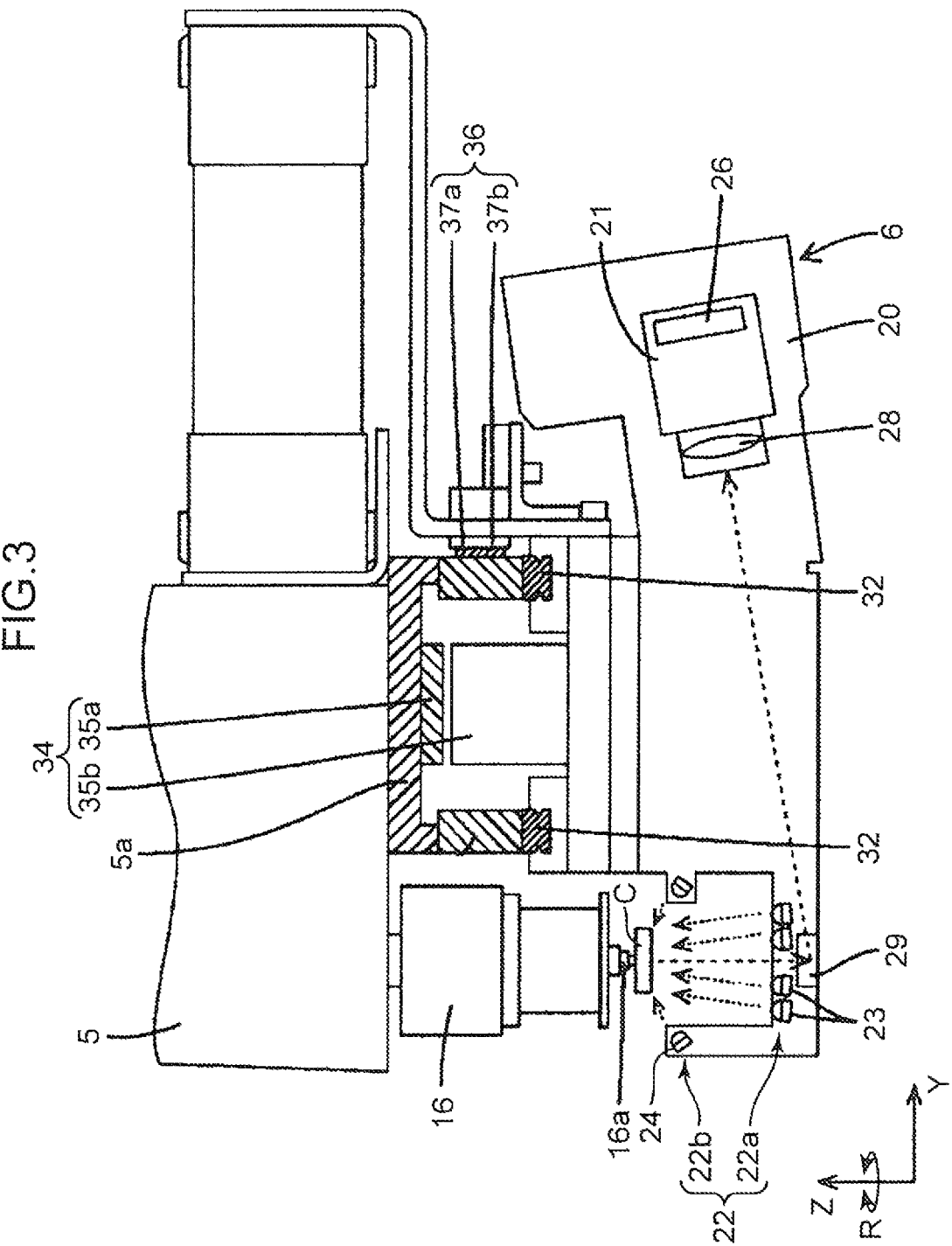

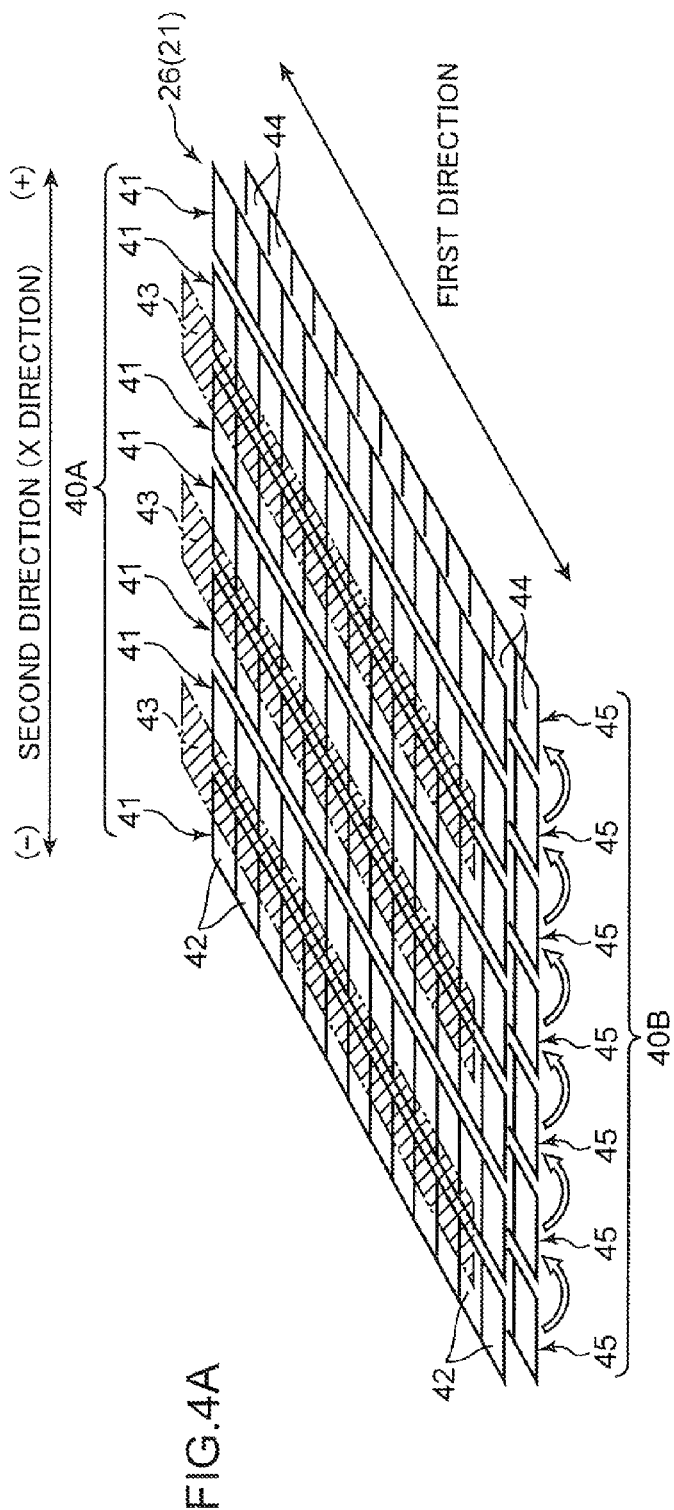
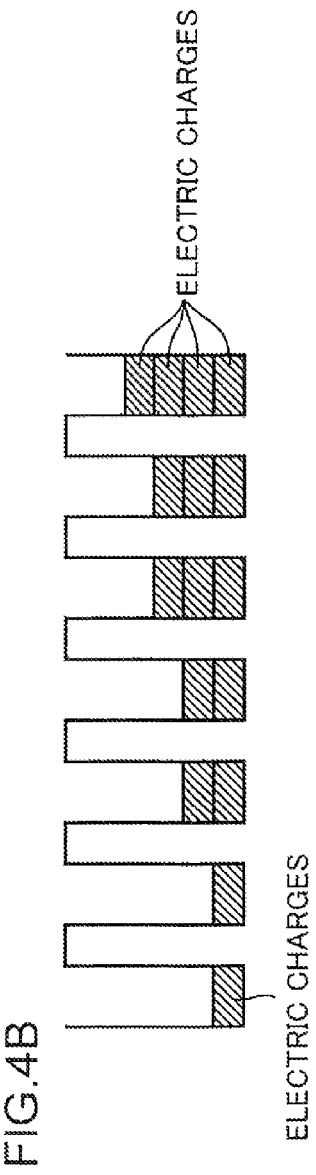
FIG.4A
FIG.4B

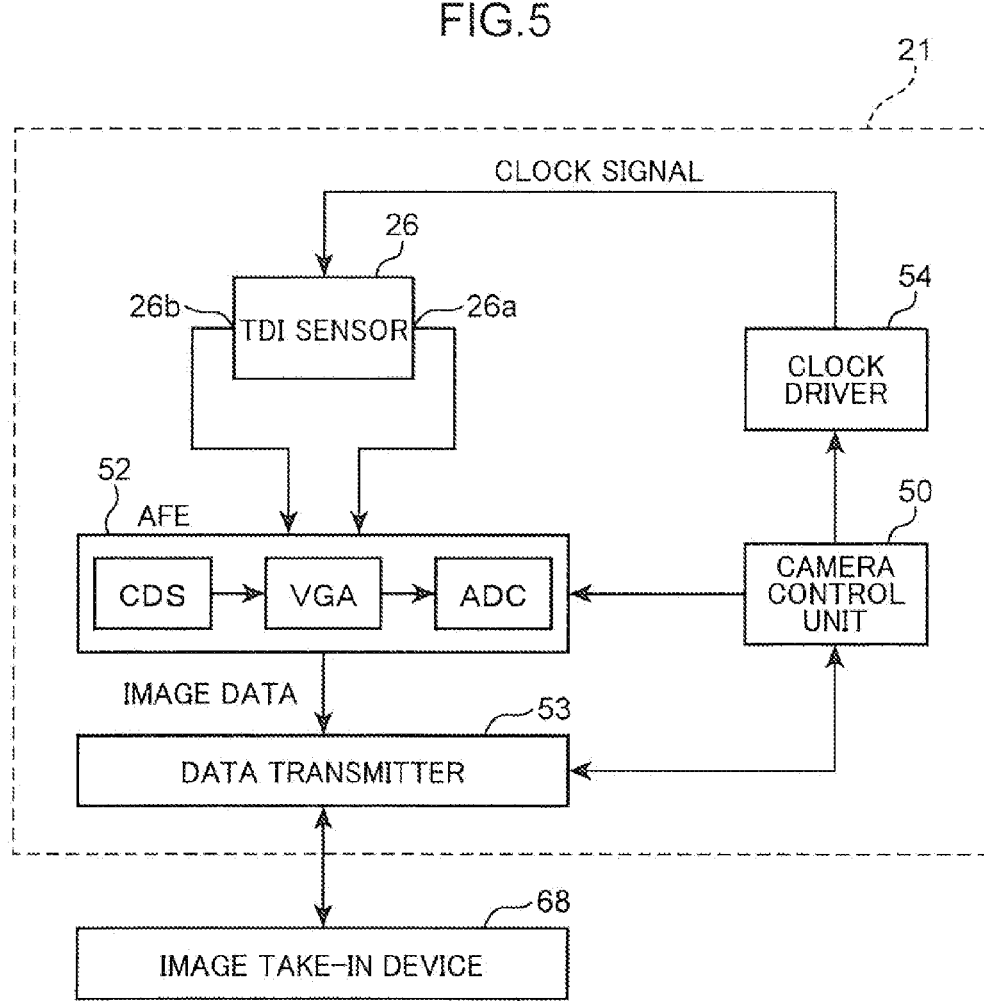

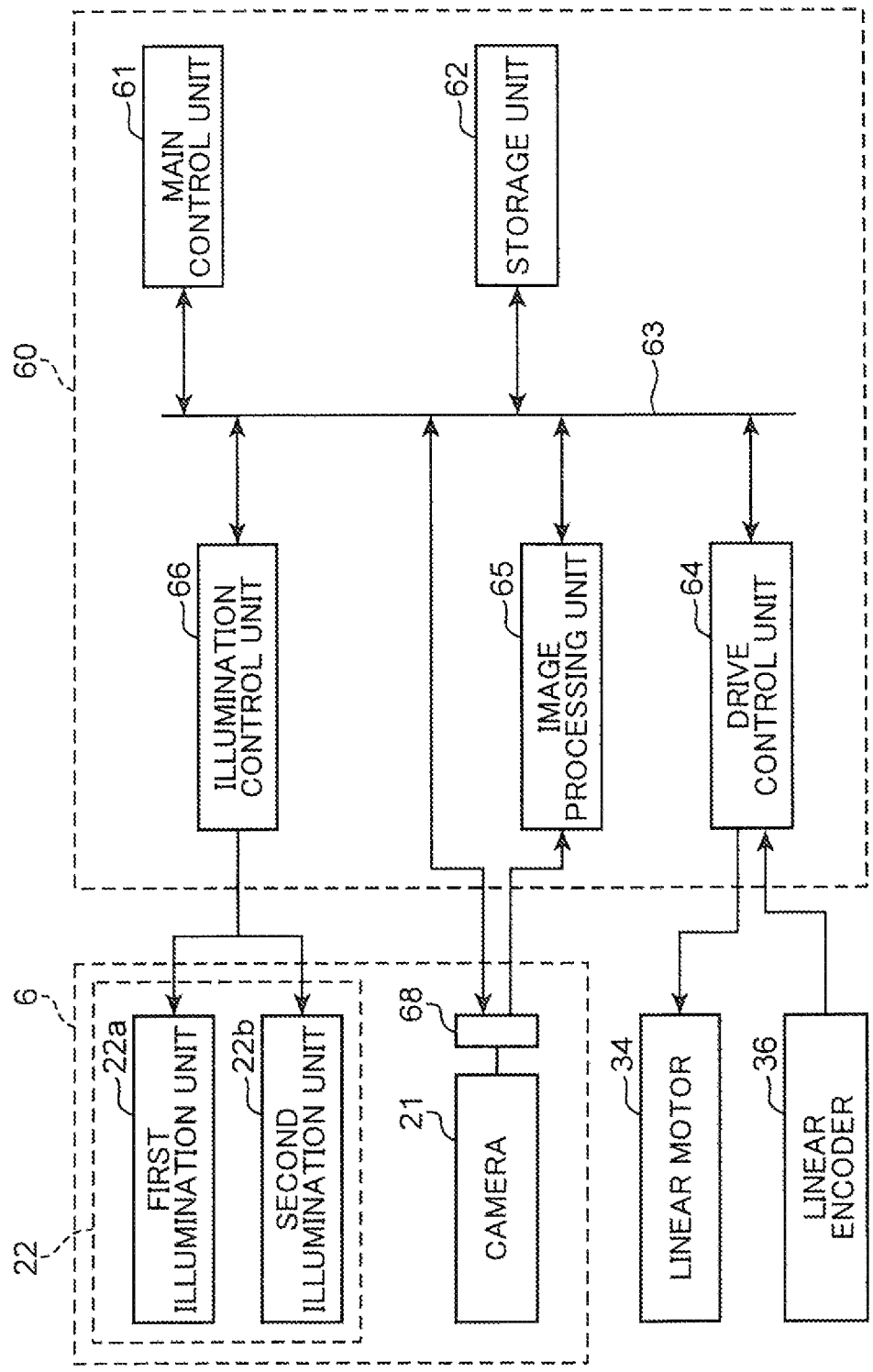

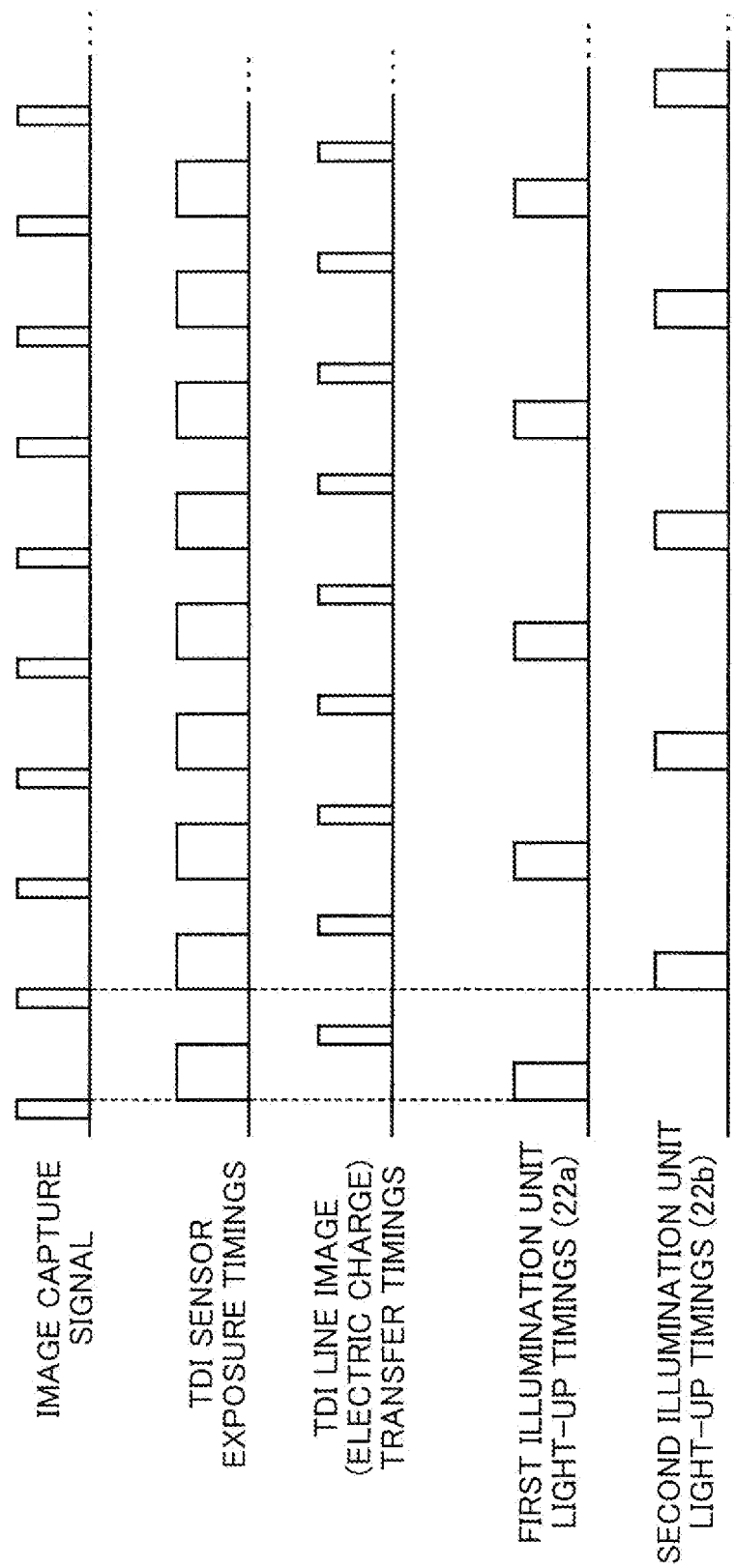

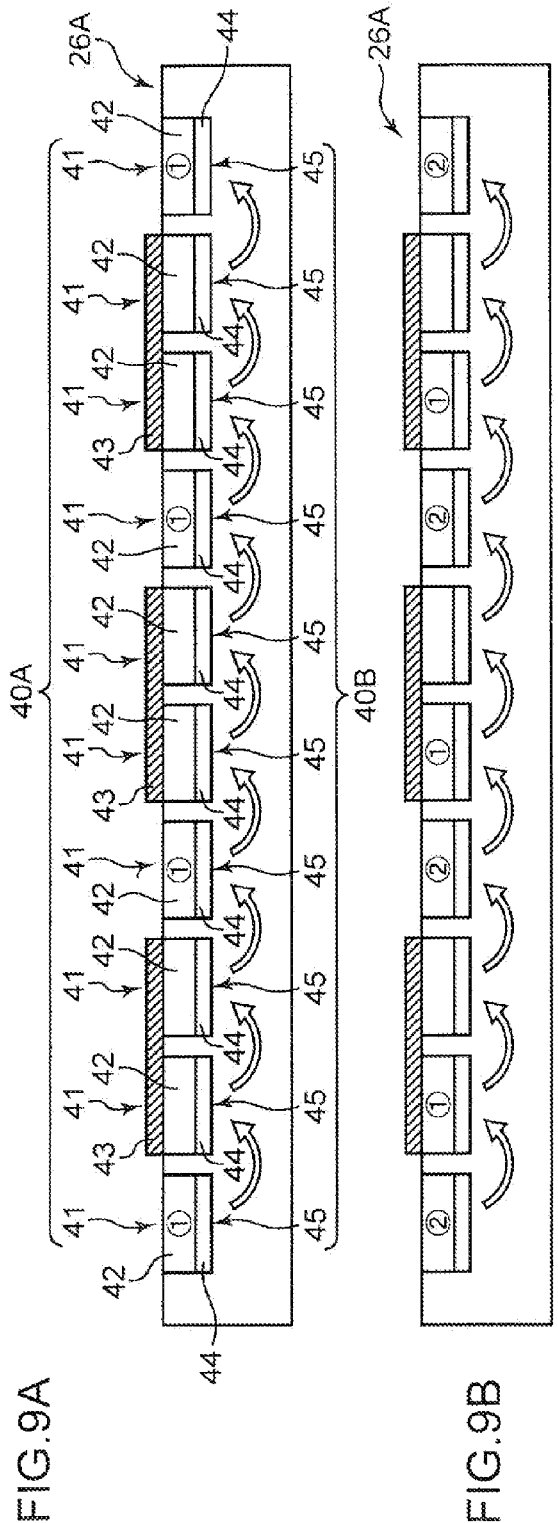
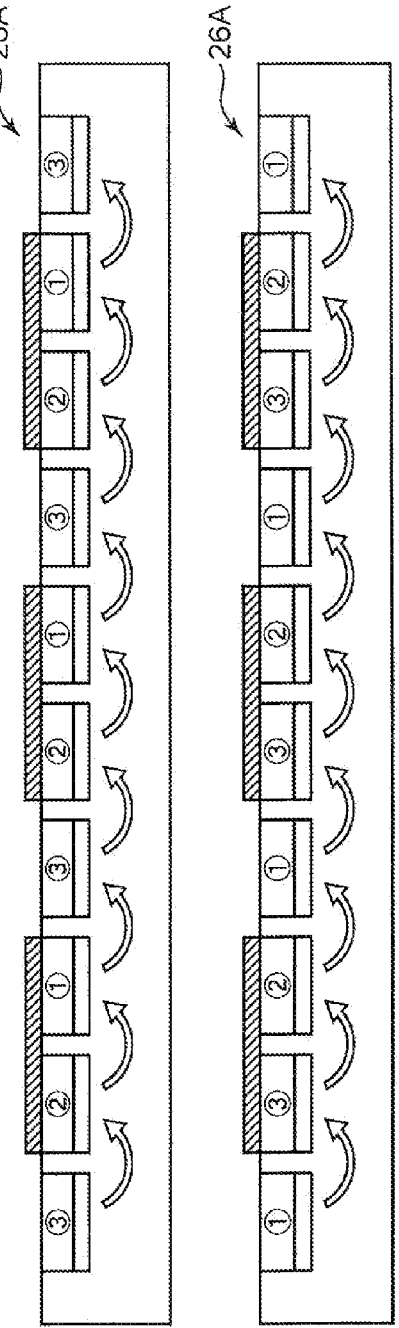
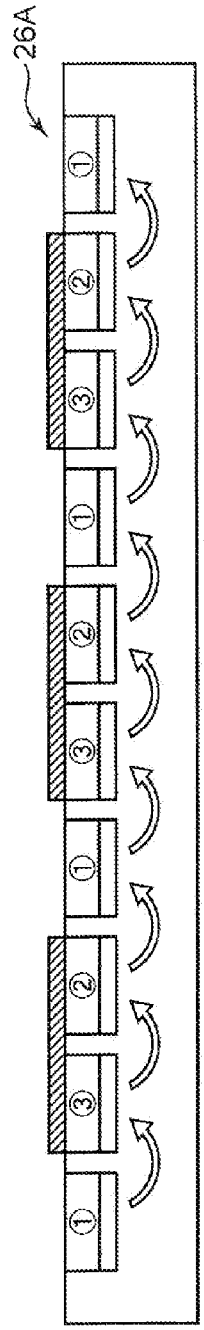

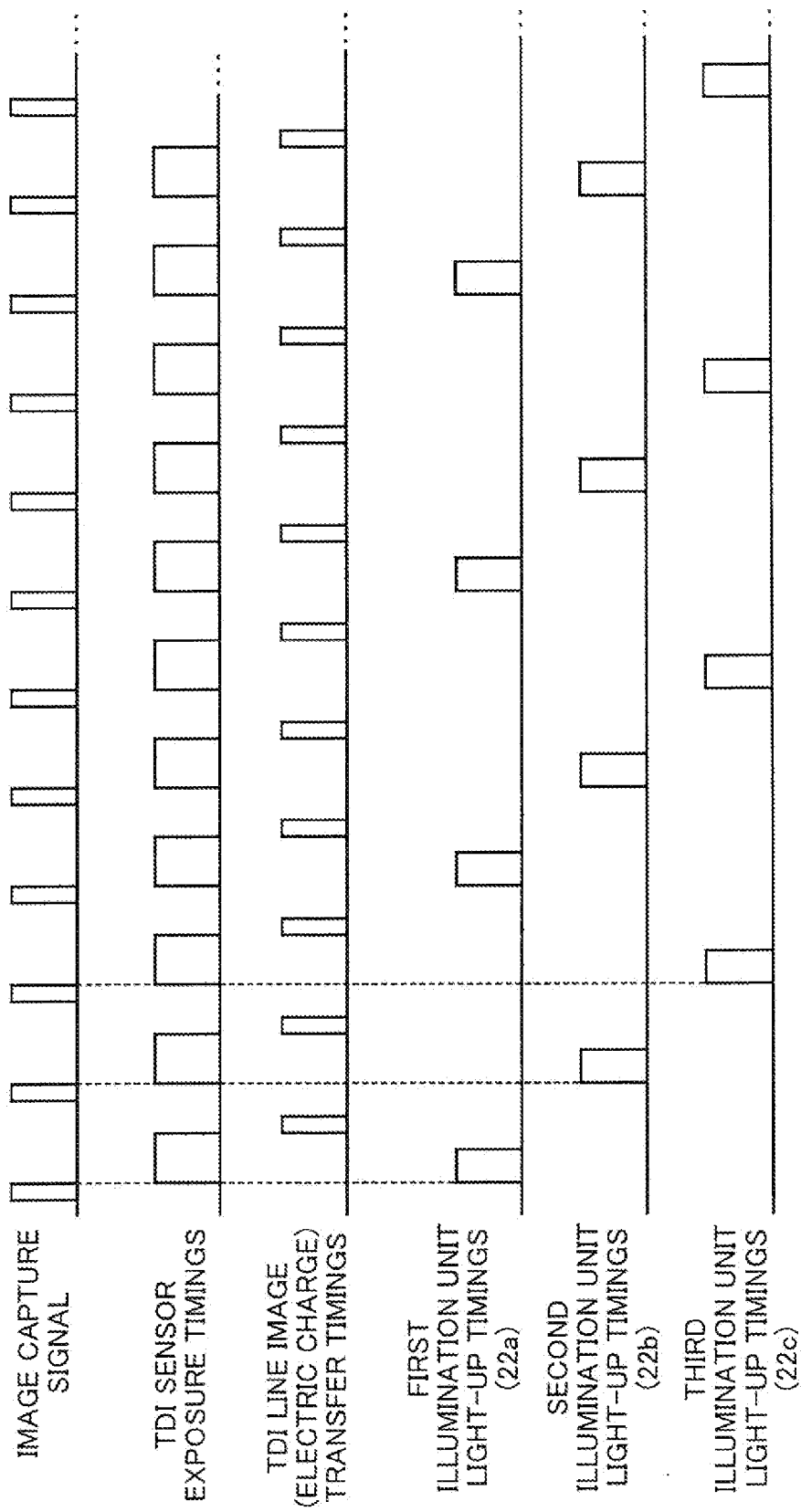

IMAGE CAPTURING APPARATUS, COMPONENT MOUNTING APPARATUS, COMPONENT TESTING APPARATUS, AND SUBSTRATE INSPECTION APPARATUS

CROSS REFERENCE TO RELATED APPLICATION

This application claims benefit of priority to International Patent Application No. PCT/JP2012/001419 filed on Mar. 1, 2012, the entire content of which is incorporated herein by reference.

TECHNICAL FIELD

The present disclosure relates to an image capturing apparatus equipped with a TDI sensor, a component mounting apparatus, a component testing apparatus and a substrate inspection apparatus that are equipped with the image capturing apparatus.

BACKGROUND

A component mounting apparatus in which a component is taken out from a component feeder by a mounting head and mounted on a mounting point on a substrate is known. The component mounting apparatus is provided with a component image capturing apparatus. This is because the image of the component held by the mounting head is captured by the component image capturing apparatus before the component is mounted on the substrate, whereby the holding state of the component by the mounting head is recognized and the component mounting posture or the like is corrected.

The component mounting apparatus of such a kind is disclosed, for example, in Japanese Patent No. 4381764. The component mounting apparatus disclosed in Japanese Patent No. 4381764 includes a component image capturing apparatus equipped with a camera for component recognition that incorporates a line sensor and a plurality of illumination units, and the component image capturing apparatus captures the image of the component by illuminating the component with one of the illumination units while moving the component at a predetermined speed relative to the camera. In this case, for a specific component, line images obtained under mutually different illumination conditions are arranged alternately, and twice as many line images are acquired by alternately switching two illumination units with different illumination conditions (illumination directions) and taking in the images while moving the components. Two component images with mutually different illumination conditions are simultaneously acquired, as the component is caused to pass only once by the camera, by extracting line images with the same illumination conditions from those images and combining the extracted images.

In the conventional component recognition apparatus such as described hereinabove, the component recognition rate apparently can be increased by increasing the movement speed of the component relative to the camera. However, where the component recognition rate is increased, the exposure time of each image capture line is shortened. As a result, the electric charge amount per each line image outputted from the line sensor is decreased and the image becomes dark and unclear. As a consequence, the component recognition accuracy can be reduced. In this case, the insufficient exposure apparently can be corrected by increasing the illumination intensity, but such a measure requires a large and expensive high-luminance illumination device, thereby increasing the size and cost of the apparatus, and cannot always be said to be effective.

In addition to the above-described acquisition of a plurality of images with different illumination conditions performed as the component is caused to pass only once by the camera, it is sometimes desirable, for example, to acquire component images of a plurality of types by receiving light beams with mutually different wavelengths under fixed illumination conditions, but such component images are difficult to acquire with the above-described component recognition apparatus.

SUMMARY

The present disclosure has been created with the foregoing in mind, and it is an object of the present intention to provide a technique capable of effectively and rapidly acquiring component images of a plurality of types by moving the object only once relative to the camera.

In order to attain such an object, the applicant focused attention on the so-called TDI sensor. The TDI sensor performs an operation of capturing a line image at predetermined timings and outputs, as an image of each image capture line, the line image exposed a plurality of times (integral exposure). Therefore, the possibility of acquiring component images, while relatively moving the component at a high speed, by using a component recognition camera equipped with the TDI sensor has been considered. However, since the TDI sensor outputs a line image subjected to integral exposure for each image capture line, line images with different illumination conditions for each image capture line are difficult to obtain by simply switching the illumination conditions during the relative movement of the component.

Accordingly, the applicant has improved the conventional TDI sensor and invented the following TDI sensor. Thus, the TDI sensor in accordance with the present disclosure is a TDI sensor that performs an operation of capturing a line image at predetermined timings and outputs as an image of each image capture line, and the line image being exposed a plurality of times. The sensor includes a light receiving unit including pixel rows each having a plurality of image capturing elements arranged in a first direction and generating and holding electric charges corresponding to respective exposure amounts. Electric charge holding rows each have a plurality of electric charge holding sections having only a function of holding the electric charges and being arranged in the first direction so as to correspond to respective image capturing elements of the pixel rows. One of the pixel rows and one or a plurality of the electric charge holding rows being alternately arranged in a second direction orthogonal to the first direction. A transfer unit sequentially, on a row-by-row basis, transfers electric charges held by the image capturing elements of the pixel rows and the electric charge holding sections of the electric charge holding rows to adjacent rows, and outputs, as a signal of the line image, a signal corresponding to electric charges finally accumulated by the transfer.

With such a TDI sensor, by switching the illumination conditions as an object moves relative to the TDI sensor, it is possible to acquire a plurality of images with different illumination conditions as the images of the object that performs the relative movement. For example, when images with two illumination conditions (taken as the first illumination condition and second illumination condition) are acquired, a sensor in which pixel rows and charge holding rows are alternately arranged can be used as the TDI sensor in accordance with the present disclosure, and two images with different illumination conditions can be acquired by alternately changing the illumination conditions as the object moves relative to the TDI sensor. Thus, the image capturing elements of each pixel row are initially exposed under the first illumination condition, following the movement of the object, whereby a line image (referred to as a first illumination image) is taken in by the pixel rows. The line images (that is, electric charges) of the pixel rows are transferred to and held by the adjacent charge holding rows before the next exposure is performed. The image capturing elements of the pixel rows are then exposed under the second illumination condition, whereby the line images (referred to as a second illumination image) is taken in by the pixel rows. The second illumination image of the pixel rows is thereafter transferred to the adjacent charge holding sections, and the first illumination image of the electric charge holdings sections is transferred to the adjacent pixel rows. Then, the image capturing elements of the pixel rows are exposed under the first illumination condition, thereby re-exposing the first illumination image in the pixel rows (electric charges are added up). As a result, a line image exposed multiple times under the first illumination condition, which is the line image of a specific single image capture line of the object, and a line image exposed multiple times under the second illumination condition, which is the line image of the following single image capture line of the object, are outputted alternately from the TDI sensor. Therefore, component images of a plurality of types can be effectively and rapidly acquired by moving the object only once relative to the TDI sensor.

BRIEF DESCRIPTION OF THE DRAWINGS

FIG. 3 is a side view of the head unit illustrating schematically the image capturing unit installed at the component mounting apparatus shown in FIG. 1.

FIG. 4A shows schematically the configuration of the TDI sensor, and FIG. 4B illustrates the electric charge accumulation state in each pixel row when the image is captured.

FIG. 5 is an electric configuration diagram of the camera.

FIG. 6 is a block diagram illustrating the principal electric configuration of the component mounting apparatus shown in FIG. 1.

FIG. 7 is a timing chart illustrating the timings of illumination, exposure (image capturing), and image (electric charge) transfer with the image capturing unit.

FIGS. 9A-9D are schematic diagrams of a TDI sensor for explaining the process of capturing three component images (FIG. 9A shows the state of the TDI sensor during the first exposure (image capturing), FIG. 9B—during the second exposure, FIG. 9C—during the third exposure, and FIG. 9D—during the fourth exposure).

FIG. 10 is a timing chart illustrating the timings of illumination, exposure (image capturing), and image (electric charge) transfer with the image capturing unit.

DETAILED DESCRIPTION

The preferred modes for carrying out the present disclosure will be described hereinbelow in greater detail with reference to the appended drawings.

First Embodiment

Figure 1:
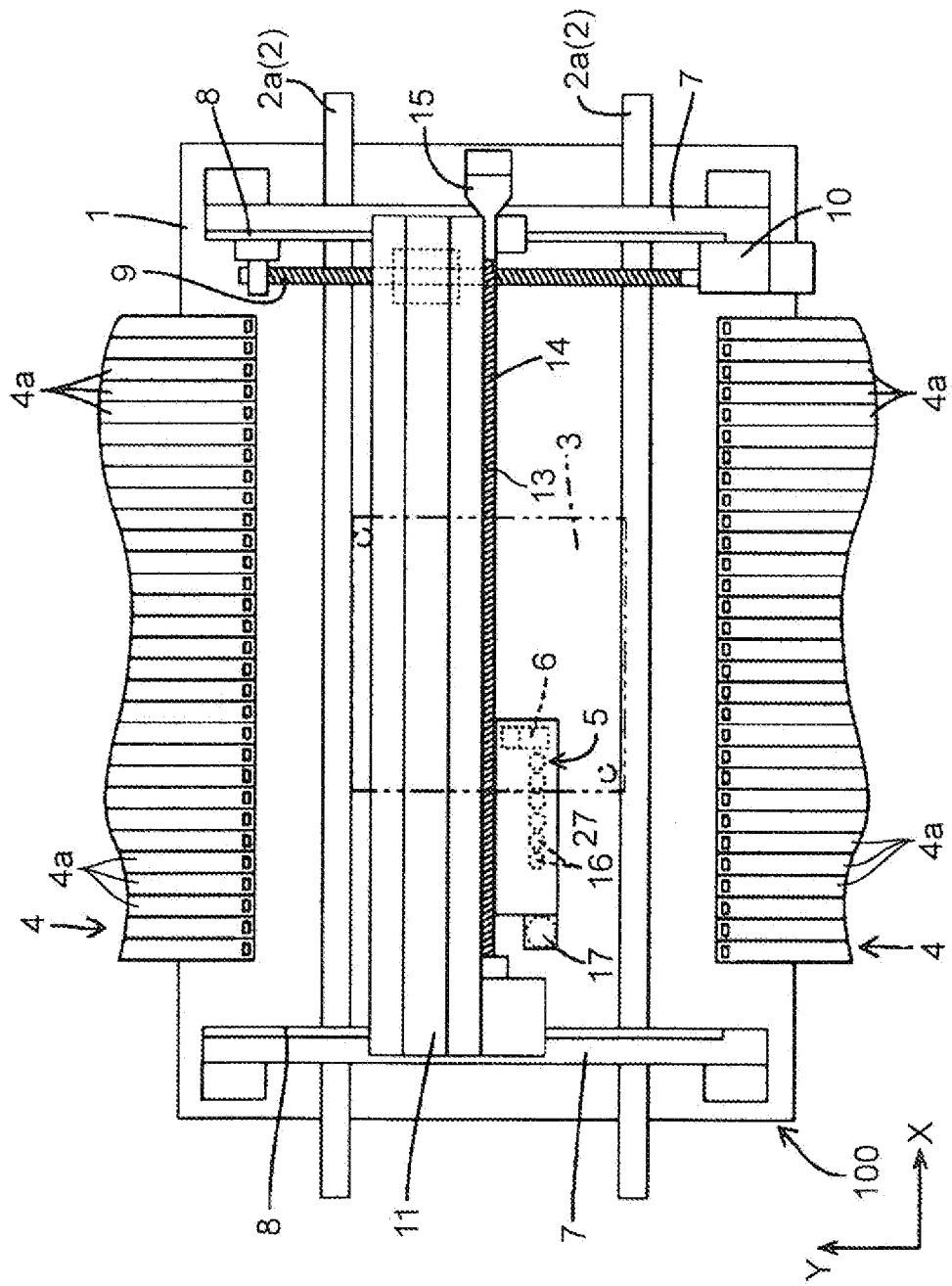
FIG. 1 is a plan view illustrating schematically the component mounting apparatus equipped with the image capturing apparatus in accordance with the present disclosure.
Figure 2:
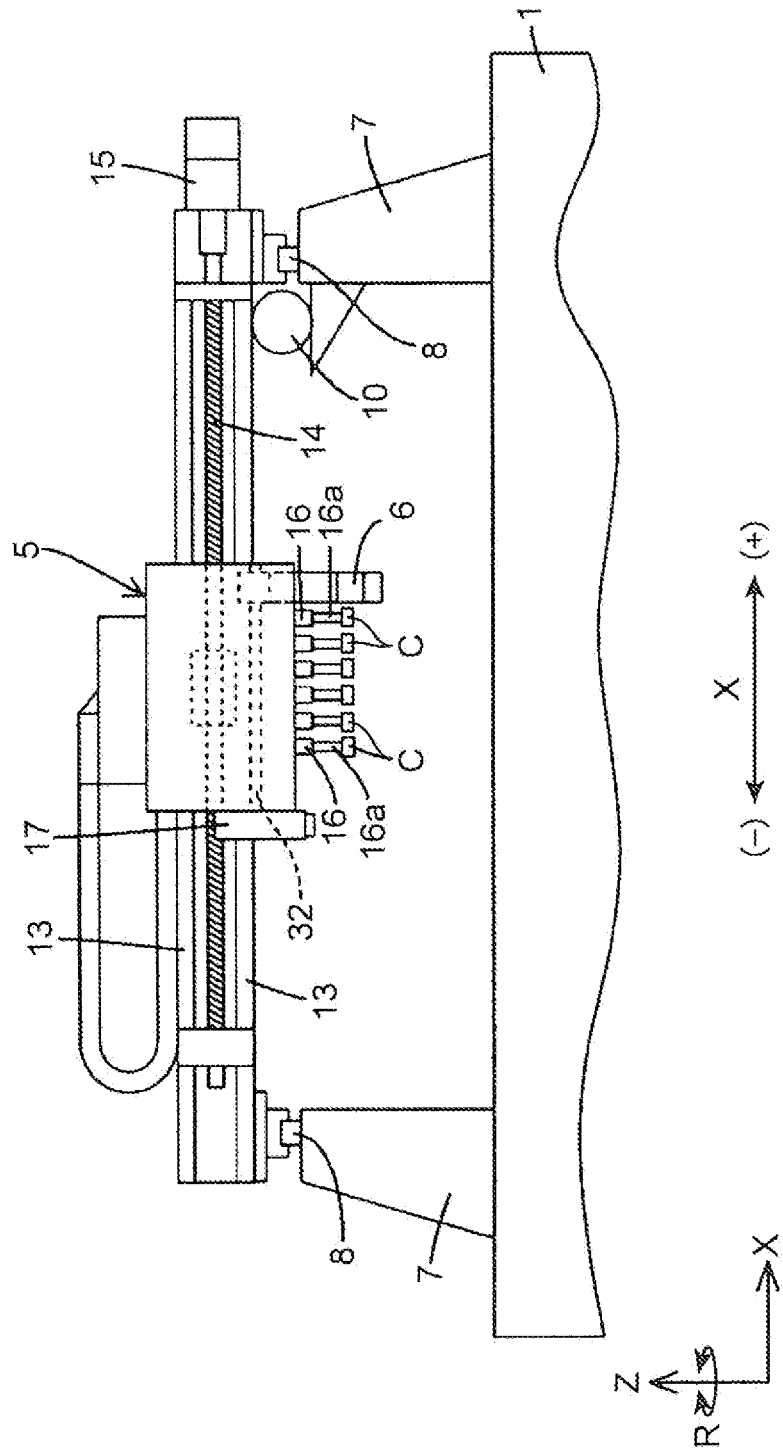
FIG. 2 is a front view illustrating schematically the component mounting apparatus shown in FIG. 1.

FIG. 1 and FIG. 2 illustrate schematically the component mounting apparatus (component mounting apparatus using the image capturing apparatus in accordance with the present disclosure) in accordance with the present disclosure. FIG. 1 is a plan view and FIG. 2 is a front view illustrating schematically the component mounting apparatus. In FIG. 1, FIG. 2, and the drawings explained hereinbelow, XYZ orthogonal coordinates are used to clarify the directional relationship in each drawing.

The component mounting apparatus is equipped with a base 1, a substrate conveying mechanism 2 that is disposed on the base 1 and conveys a substrate 3 such as a printed wiring board (PWB) in the X direction, component feeding units 4, a head unit 5 for component mounting, a head unit drive mechanism that drives the head unit 5, and an image capturing unit 6 for component recognition.

The substrate conveying mechanism 2 includes a pair of conveyors 2a that convey the substrate 3 on the base 1. The conveyors 2a receive the substrate 3 from the right side, as shown in the figure, convey the substrate to a predetermined mounting operation position (position shown in the figure), and hold the substrate 3 with a holding device (not shown in the figure). After the mounting operation, the substrate 3 is carried out to the left side, as shown in the figure.

The component feeding unit 4 is disposed at each side (each side in the Y direction) of the substrate conveying mechanism 2. A plurality of tape feeders 4a arranged side by side in the X direction are disposed along the substrate conveying mechanism 2 in each of the component feeding units 4. Each tape feeder 4a is equipped with a reel having wound thereon a tape that accommodates and holds a small chip component such as an IC, a transistor, and a capacitor. The component is fed to a predetermined component feeding position close to the substrate conveying mechanism 2 by intermittently paying out the tape from the reel. Instead of the tape feeders 4a, either or both of the component feeding units 4 may have set therein a tray in which package-type components such as a QFP (Quad Flat Package) or a BGA (Ball Grid Array) are orderly arranged.

The head unit 5 takes out a component from the component feeding unit 4 and mounts the component on the substrate 3. The head unit is disposed above the substrate conveying mechanism 2 and the component feeding units 4.

The head unit 5 can be moved by the head unit drive mechanism in the X direction and Y direction in a predetermined region. The head unit drive mechanism includes an Y-axis servo motor 10, a pair of fixed rails 8 that are fixed respectively to a pair of high-beam frames 7, which are provided on the base 1, and extend parallel to each other in the Y direction, a unit support member 11 that is supported on those fixed rails 8 and extends in the X direction, and a ball screw shaft 9 that is screwed into the unit support member 11 and driven by the Y-axis servo motor 10. Included also are an X-axis servo motor 15, a fixed rail 13 fixed to the unit support member 11 and supporting the head unit 5 to enable the movement thereof in the X direction, and a ball screw shaft 14 that is screwed into the head unit 5 and driven by the X-axis servo motor 15 as a drive source. Thus, in the head unit drive mechanism, the head unit 5 is moved in the X direction by the drive of the X-axis servo motor 15 through the ball screw shaft 14, and the unit support member 11 is moved in the Y direction by the drive of the Y-axis servo motor 10 through the ball screw shaft 9. As a result, the head unit 5 is moved in the X direction and Y direction within a predetermined region.

The head unit 5 is equipped with a plurality of mounting heads 16, each being provided with a nozzle 16a for component attachment at a tip thereof, and a head drive mechanism using a servo motor as a drive source for lifting (movement in the Z direction) those mounting heads 16 with respect to the head unit 5 and rotating (rotation in the R direction in FIG. 2 and FIG. 3) the mounting heads about the central axis of the nozzle.

A total of six mounting heads 16 are installed on the head unit 5 in a state of arrangement in a row in the X direction. A nozzle 16a of each mounting head 16 can be communicated with by a respective electric switching valve to a negative pressure generator, a positive pressure generator, and the atmosphere. In other words, a component can be attached to and held by the nozzle 16a when a negative pressure is supplied to the nozzle 16a, and the attachment and holding of the component can be canceled by thereafter supplying a positive pressure.

The image capturing unit 6 for recognizing components C attached to and held by the mounting heads 16, a unit drive mechanism that drives the image capturing unit 6, and a substrate recognition camera 17 for recognizing the substrate 3 are installed on the head unit 5.

The substrate recognition camera 17 is fixed to one end (left end in the example shown in FIG. 1 and FIG. 2), in the X direction, of the head unit 5. The substrate recognition camera 17 captures an image of various marks provided on the substrate 3 in order to specify the position of the substrate 3 aligned at the mounting operation position or the mounting operation contents. In the substrate recognition camera 17, a camera main body including an area sensor and a condensing lens is provided integrally with an illumination device, and the image of the mark is captured by radiating illumination light from above on the substrate 3 and receiving the reflected light therefrom by the area sensor.

As shown in FIG. 3, the image capturing unit 6 includes a camera 21 that captures the image of the components C, an illumination device 22 (corresponds to the illumination device in accordance with the present disclosure) that illuminates the components C for image capturing, a reflecting mirror 29 that reflects the image of the components C so that it could be captured by the camera 21, and a casing 20 integrally holding the camera 21, the illumination device 22, and the reflecting mirror 29.

The camera 21 includes a TDI (Time Delay Integration) sensor 26 and a condensing lens 28 and is arranged substantially in the transverse direction. The camera 21 captures the image of the components C by forming, with the condensing lens 28, the image of the reflected light from the components C, which is obtained by the illumination for image capturing, on a light receiving unit 40A (see FIG. 4) of the TDI sensor 26. The camera 21 including the TDI sensor 26 will be explained hereinbelow in greater detail.

The illumination device 22 is attached to the casing 20 so that the illumination device could be disposed below the mounting heads 16 disposed at a predetermined component recognition height position.

The illumination device 22 includes a first illumination unit 22a that illuminates the components C from below, and a second illumination unit 22b that illuminates the components C from a side. The first illumination unit 22a is provided with a plurality of LEDs 23 arranged to face upward, and where the LEDs 23 are lighted, the components C attached to and held by the mounting heads 16 are illuminated from below with the illumination light. Meanwhile, the second illumination unit 22b is disposed above the first illumination unit 22a. The second illumination unit 22b includes a plurality of LEDs 24 facing inward towards each other in the Y direction. Where the LEDs 24 are lighted, the component C is illuminated from the side thereof and somewhat obliquely from below with the illumination light.

The reflecting mirror 29 is disposed at a position facing the mounting heads 16. As a result, the reflected light from the components C falls on the camera 21 after the direction of the light is changed by the reflecting mirror 29 into a direction close to the horizontal direction. The LEDs 23 of the first illumination unit 22a are disposed to surround the reflecting mirror 29.

The unit drive mechanism that drives the image capturing unit 6 includes fixed rails 32 that are fixed to a bottom frame 5a of the head unit 5 and support the casing 20 so that the casing can move in the X axis direction, a linear motor 34 as a drive source, and a linear encoder 36.

The linear motor 34 includes a permanent magnet 35a as a stator fixed to the bottom frame 5a along the X direction, and a coil section 35b serving as a movable element that is fixed to the casing 20 so as to face the permanent magnet 35a at a predetermined distance therefrom. Where the coil section 35b is energized, a propulsion force in the X direction is applied to the casing 20. With such a configuration, the image capturing unit 6 moves in the X direction along the fixed rails 32.

The linear encoder 36 includes a magnetic scale 37a fixed to the bottom frame 5a along the X direction, and a magnetic sensor 37b, such as an MR sensor or a Hall sensor, fixed to the casing 20 so as to face the magnetic scale 37a. Scale marks are magnetically recorded in the magnetic scale 37a, and the magnetic sensor 37b detects the scale marks and outputs electric signals corresponding to the scale marks to a below-described control device 60.

Thus, the image capturing unit 6 is configured such that the image of the components C attached to and held by the mounting heads 16 can be sequentially captured by the camera 21 as the image capturing unit 6 is moved in the X direction by the drive of the linear motor 34. In this case, the position and movement speed of the image capturing unit 6 are controlled by the below-described control device 60 on the basis of the output signals from the linear encoder 36.

FIG. 4A shows schematically the configuration of the TDI sensor 26 provided in the camera 21. As shown in the figure, the TDI sensor 26 includes a light receiving unit 40A and a transfer section 40B.

The light receiving unit 40A includes a plurality of pixel rows 41 in which a plurality of image capturing elements 42, which generate and hold an electric charge corresponding to the received quantity of light, is arranged in a row in a first direction. The pixel rows 41 are arranged in a second direction orthogonal to the first direction. The light receiving unit 40A includes an odd number of the pixel rows 41. In the example shown in the figure, the number of pixel rows 41 is 7, for convenience sake, but the number of the pixel rows 41 and the number of pixels in each pixel row 41 (number of image capturing elements 42) are actually determined to obtain the desired resolution. For example, the number of pixel rows can be set to about 150.

The transfer section 40B includes a plurality of register rows 45 corresponding to respective pixel rows 41. Each register row 45 includes a plurality of registers 44 each forming a pair with the respective image capturing element 42 of the corresponding pixel row 41. Each register 44 has a function of reading the electric charge of the image capturing element 42 forming a pair therewith, and sequentially transferring the electric charge that has been read to the image capturing element 42 of the adjacent pixel row 41. The electric charge transfer direction can be switched. In the figure, outline arrows illustrate the case in which the read-out electric charge is transferred to the image capturing element 42 of the pixel row 41 adjacent at the (+) side in the second direction.

Among the plurality of pixel rows 41 in the light receiving unit 40A, those with odd numbers (odd-numbered rows), when counted from one end in the arrangement direction thereof, are the pixel rows 41 that can receive light by the image capturing elements 42, and those with even numbers (even-numbered rows) are the pixel rows 41 in which the image capturing elements 42 cannot receive light because light-blocking filters 43 (corresponding to the light-blocking sections in accordance with the present disclosure) are formed on the surface of the image capturing elements 42. As a result, in the image capturing elements 42 belonging to the even-numbered pixel rows 41, no electric charges are generated by the received light, and those image capturing elements 42 have only the function of holding the electric charges transferred from the image capturing elements 42 of the adjacent pixel rows 41. In the present example, the pixel rows 41 belonging to the even-numbered rows correspond to the electric charge holding rows in accordance with the present disclosure, and the image capturing elements 42 where the light-blocking filters 43 are formed correspond to the electric charge holding sections in accordance with the present disclosure. Meanwhile, the image capturing elements 42 belonging to the odd-numbered pixel rows 41 have a function of adding the electric charges generated by light reception to the electric charges transferred from the image capturing elements 42 of the adjacent pixel rows 41 and holding the resultant electric charges.

The camera 21 is installed on the image capturing unit 6 so that the arrangement direction (second direction) of the pixel rows 41 of the TDI sensor 26 is parallel to the X direction. As a result, where the image capturing unit 6 moves in the X direction, electric charges corresponding to the reflected light from the components C are generated in the image capturing elements 42 of the odd-numbered pixel rows 41, from among the pixel rows 41 of the light receiving unit 40A. In other words, the line images of each single image capture line of the components C are sequentially taken in by the image capturing elements 42 of the odd-numbered pixel rows 41.

The operation of capturing the images of the components C with the camera 21 is explained below with respect to a case in which the images of the components C are captured while the image capturing unit 6 moves from the (+) side to the (−) side in the X direction.

The images of the components C are captured by exposing the image capturing elements 42 of each pixel row 41 at a fixed image capture timing synchronized with the movement of the image capturing unit 6 under the illumination with the illumination device 22 in a state in which the movement speed of the image capturing unit 6 is controlled to a constant value by the control device 60. In this case, the first illumination unit 22a and the second illumination unit 22b are lighted alternately.

More specifically, the exposure is performed at a timing at which the image capturing unit 6 moves by a row arrangement pitch p of the pixel rows 41 (the timing at which the components C move by the row arrangement pitch p relative to the image capturing unit 6). Due to such exposure, a line image of a single image capture line of the components C is taken in by the odd-numbered pixel rows 41 in which no light-blocking filters 43 are formed, from among the pixel rows 41. Thus, as a result of such exposure, the reflected light from the components C falls on the image capturing elements 42 of each pixel row 41, whereby an electric charge corresponding to the received quantity of light is generated in each image capturing element 42.

For example, the first illumination unit 22a is initially lighted, and in this case a timing at which a site at a distance L (L<=p) from the distal end section, in the relative movement direction, of the components C moving relative to the image capturing unit 6 (this site will be simply referred to hereinbelow as the "distance-L site of the components") reaches a position facing the first pixel row 41, with the reflecting mirror 29 being interposed therebetween, and the exposure initially performed is taken as a first timing.

In this case, the electric charge (line image of the distance-L site of the components C) generated by the leading (first) pixel row 41, from among the pixel rows 41 of the light receiving unit 40A, is read by the register 44 of the register row 45 corresponding to this pixel row 41 and transferred to the image capturing elements 42 of the adjacent second pixel row 41. Where the image capturing unit 6 moves by the row arrangement pitch p, a distance-(L+p) site of the components reaches a position facing the first pixel row 41, with the reflecting mirror 29 being interposed therebetween, and at this timing (taken as a second timing), the image capturing elements 42 of each pixel row 41 are exposed by lighting the second illumination unit 22b. However, since the light-blocking filters 43 have been formed, as mentioned hereinabove, at the image capturing elements 42 of the second pixel row 41, no electric charge is generated in this pixel row 41. Therefore, the electric charge generated by the exposure at the first timing (line image at the first timing of the distance-L site of the components C) is transferred to and held in the image capturing elements 42 of the second pixel row 41, and the electric charge generated by the exposure at the second timing (line image of the distance-(L+p) site of the components C) is held in the image capturing elements 42 of the first pixel row 41.

Where the image capturing unit 6 moves further, the electric charge (line image) of the second pixel row 41 is read, synchronously with the movement, to the register 44 of the register row 45 corresponding to the pixel row 41 and transferred to the image capturing elements 42 of the adjacent third pixel row 41. Where the image capturing unit 6 moves by the row arrangement pitch p, the distance-(L+2 p) site of the components C reaches a position facing the first pixel row 41, with the reflecting mirror 29 being interposed therebetween, whereas the distance-L site of the components C reaches a position facing the third pixel row 41, with the reflecting mirror 29 being interposed therebetween, and at this timing (third timing), the image capturing operation is executed by lighting the first illumination unit 22a, whereby an electric charge corresponding to the received quantity of light (line image at the third timing of the distance-L site of the components C) is generated in the image capturing elements 42 of the third pixel row 41. In other words, the electric charge (line image at the third timing of the distance-L site of the components C) newly generated in the image capturing elements 42 of the third pixel row 41 is added to the electric charge (line image at the first timing of the distance-L site of the components C) transferred from the second pixel row 41 to the third pixel row 41. Thus, a sum total of the electric charge created by the exposure at the first timing of the distance-L site of the components C (exposure by the first illumination unit 22a) and the electric charge created by the exposure at the third timing (exposure by the first illumination unit 22a) is held in the third pixel row 41. Meanwhile, the electric charge created by the exposure at the second timing of the distance-(L+p) site of the components C (exposure by the second illumination unit 22a) is held in the image capturing elements 42 of the second image row 41, and the electric charge created by the exposure at the third timing of the distance-(L+2 p) site of the components C is held in the image capturing elements 42 of the first pixel row 41.

Similar operations are thereafter repeatedly performed in the pixel rows 41, following the movement of the image capturing unit 6. As a result, as shown in FIG. 4B, the electric charges are sequentially added up and accumulated in the odd-numbered pixel rows 41 with respect to the same image capture line of the components C. In other words, the line image of the same image capture line of the components C is repeatedly exposed in the odd-numbered pixel rows 41. Further, the accumulated electric charges for the single image capture line that has been exposed by lighting the first illumination unit 22a at the odd-numbered image capture timings and the electric charges for the single image capture line that has been exposed by lighting the second illumination unit 22a at the even-numbered image capture timings are read alternately from the pixel rows 41 at the (+)-side end in the X direction into the corresponding register rows 45, and signals corresponding to the accumulated electric charges for a single image capture line at each site of the components C are alternately and sequentially outputted from the TDI sensor 26. The electric charges created by image capturing at different timings and under different illumination conditions at the odd-numbered single image capture lines and the even-numbered single image capture lines are sequentially accumulated for a single image capture line for each pitch p (distance equal to the row arrangement pitch p of the pixel rows 41) in the component C, following the movement of the image capturing unit 6, and alternately outputted from the TDI sensor 26. In other words, the line images of the single image capture lines for each pitch p in the components C which are obtained by multiple exposures at timings and under illumination conditions which differ among the adjacent single image capture lines are sequentially outputted from the TDI sensor 26 over the entire length of the components C. As a result, component images of two types that differ in illumination conditions and are constituted by a line image group of single image capture lines for every 2 pitches (2 p) of the components C are obtained. This feature is explained hereinbelow in greater detail with reference to FIG. 8 or the like.

In the case explained hereinabove, the image capturing unit 6 moves from the (+) side to the (−) side in the X direction, but the case in which the image capturing unit 6 moves from the (−) side to the (+) side in the X direction is basically the same. In this case, the pixel row 41 at the (+) side end in the X direction is taken as the leading (first) pixel row 41, the electric charges are accumulated and transferred, and the electric charge corresponding to the line image of a single image capture line of the components C is outputted from the register row 45 corresponding to the pixel row 41 at the (−) side end in the X direction. Therefore, the TDI sensor 26 is provided with two output units 26a, 26b (see FIG. 5) corresponding to the electric charge transfer direction as the output units for the signals.

FIG. 5 illustrates the principal electrical configuration of the camera 21. As shown in the figure, the camera 21 includes a camera control unit 50, an analog front end (AFE) 52, a data transmitter 53, and a clock driver 54 in addition to the TDI sensor 26.

The camera control unit 50 controls integrally the operation of the camera 21 on the basis of control signals received from the below-described control device 60 via an image take-in device 68. For example, the TDI sensor 26 is provided with two output units 26a, 26b for outputting image data corresponding to the scanning direction (movement direction of the image capturing unit 6 with respect to the component C), and the camera control unit 50 switches the transfer direction of electric charges in the TDI sensor 26 corresponding to the scanning direction by changing a clock signal from the clock driver 54, as described hereinbelow, so that the image data is outputted from either of the two output units 26a, 26b.

The analog front end 52 sets a camera gain by a control signal from the camera control unit 50, adjusts the output value of image data on the basis of the camera gain, and converts the image data (analog data) into digital image data. The analog front end 52 includes a correlated double sampler (CDS), a variable gain amplifier (VGA), an AD converter (ADC; analog to digital converter) and the like.

The data transmitter 53 performs signal transmission and reception with the other devices. For example, the data transmitter 53 transmits the image data received from the analog front end 52 to the below-described control device 60 through the image take-in device 68, receives a signal from the control device 60 through the image take-in device 68, and transmits the received signal to the camera control unit 50. In other words, the image take-in device 68 has a function of an interface that converts the signals transmitted between the camera 21 and the control device 60 into reciprocally readable signals.

The clock driver 54 outputs a clock signal to the TDI sensor 26 on the basis of a control signal corresponding to the scanning direction that is inputted from the camera control unit 50, and controls the timing of image capture (exposure) by the TDI sensor 26 and the transfer timing and transfer direction of the electric charge (line image) of each pixel row 41. The clock signal includes information corresponding to the scanning direction, and the TDI sensor 26 switches the accumulation and transfer direction of the electric charges on the basis of this information.

The component mounting apparatus further includes the control device 60, such as shown in FIG. 6, for controlling the operation thereof. The control device 60 includes a main control unit 61 that performs integrated control of operations of the entire component mounting apparatus, a storage unit 62 that stores various processing programs and various data, a drive control unit 64 that controls the drive of the head unit 5, the image capturing unit 6 or the like, an image processing unit 65, and an illumination control unit 66. The control device is configured such that those units are connected by a bus 63 to enable signal exchange therebetween.

The main control unit 61 controls the drive control unit 64, image processing unit 65, illumination control unit 66, and camera 21 according to the mounting program stored in the storage unit 62, and also performs image recognition of the components C attached to the mounting heads 16 or various types of image processing and computational processing necessary therefor, and causes the storage unit 62 to store image data. In particular, when component recognition is performed, the main control unit acquires images of two types that differ in illumination conditions, more specifically, the first component image obtained by lighting only the first illumination unit 22a and the second component image obtained by lighting only the second illumination unit 22b, while the image capturing unit 6 is scanned only once with respect (moved relative to) the components C attached to the mounting heads 16, controls the movement speed of the image capturing unit 6 to recognize the holding state of the components C by the mounting heads 16 on the basis of the first component image and second component image, and controls the image capture timing of the components C or the lighting timing of the illumination device 22 on the basis of the timing chart (FIG. 7) stored in the storage unit 62.

In the present embodiment, the image capturing unit 6, unit drive mechanism, control unit 60 and the like correspond to the image capturing device in accordance with the present disclosure. Among them, the unit drive mechanism corresponds to the drive device for the image capturing device. The main control unit 61, illumination control unit 66, camera control unit 50 and the like correspond to the image capture control device in accordance with the present disclosure. Further, the head unit drive mechanism, the control device 60 and the like correspond to the forwarding device in accordance with the present disclosure.

A series of mounting operations performed with the component mounting apparatus on the basis of control by the control device 60 is explained below, and then the control of image capturing and recognition processing of the components C based on the timing chart shown in FIG. 7 is explained.

In the component mounting apparatus, first, the head unit 5 moves above the component feeding unit 4, and the components are attached and held by the mounting heads 16 (nozzles 16a). In this case, as shown in FIG. 2, the image capturing unit 6 is disposed at a predetermined standby position outside of the arrangement region of the mounting heads 16. As a result the image capturing unit does not hinder the component attachment operation performed by the mounting heads 16. In the present embodiment, the positions at both sides on the outside of the arrangement region of the mounting heads 16 in the X direction are taken as the standby positions (the (+) side in the X direction is taken as the first standby position, and the (−) side is taken as the second standby position). In the example shown in FIG. 2, the image capturing unit 6 is disposed at the first standby position.

Once the attachment of the component is completed, the head unit 5 starts moving to a position above the substrate 3. As the head unit 5 moves, the image capturing unit 6 moves at a constant speed in the X direction from the first standby position towards the second standby position immediately below the components C that are attached to and held by the mounting heads 16, whereby the images of the components C are captured, and the attachment state of the components C held by the mounting heads 16 is recognized on the basis of the image data. In this case, since each mounting head 16 is disposed at the component recognition height position above the region through which the image capturing unit 6 passes, as shown in FIG. 2 and FIG. 3, the image capturing unit 6 is moved and the images of the components C are captured without hindrance.

When there is a defective component or a component in an attachment state that cannot be corrected among the components C held by the mounting heads 16, this component C is registered as a reject object, the head unit 5 moves above the substrate 3, and the components C other than the reject object are sequentially mounted on the substrate 3. In this case, the components can be adequately mounted at the respective installation positions on the substrate 3 by controlling the position of the head unit 5 and the rotation angle of the mounting heads 16 according to the recognition results relating to the components C.

Where the components C are thus mounted on the substrate 3, the head unit 5 moves to a position above a component reject box (not shown in the figure), and the component C which is the reject object is discarded. A cycle of the mounting operation is thus completed and, if necessary, the required components C are mounted on the substrate 3 by repeating this operation.

FIG. 7 is a timing chart illustrating the control of the camera 21 and the illumination device 22.

Where the image capturing unit 6 starts moving, the main control unit 61 outputs image capture signals to the camera 21 (camera control unit 50) and the illumination control unit 66 at predetermined timings on the basis of the output signals from the linear encoder 36. More specifically, the image capturing unit 6 repeatedly outputs image capture signals at each timing at which the image capturing unit moves by the arrangement pitch p of the pixel rows 41 of the TDI sensor 26.

Where the image capture signal is inputted to the illumination device 22, the illumination device 22 is lighted for a fixed period of time on the basis of the inputted image capture signal. Meanwhile, the camera control unit 50 outputs a control signal to the clock driver 54, and a clock signal is outputted from the clock driver 54 to the TDI sensor 26, thereby causing the TDI sensor 26 to execute the image capturing operation. More specifically, the image capturing elements 42 of each pixel row 41 are exposed for a fixed period of time, and after the exposure is completed, the electric charges generated in the pixel rows 41 are transferred to the adjacent pixel rows 41.

In this case, each time the illumination device 22 inputs the image capture signal from the main control unit 61, the first illumination unit 22a and the second illumination unit 22b are switched. By so switching the first illumination unit 22a and the second illumination unit 22b each time the image capture signal is inputted, it is possible to acquire the first component image and the second component image within a single scan of the component C by the image capturing unit 6.

Figure 8A:
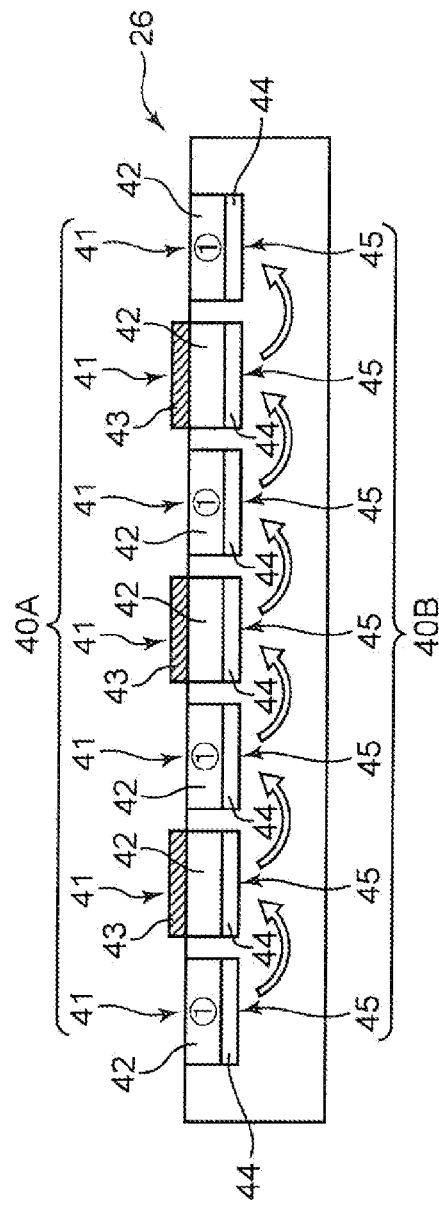
FIGS. 8A-8C are schematic diagrams of a TDI sensor for explaining the process of capturing two component images (FIG. 8A shows the state of the TDI sensor during the first exposure (image capturing), FIG. 8B—during the second exposure, and FIG. 8C—during the third exposure).
Figure 8B:
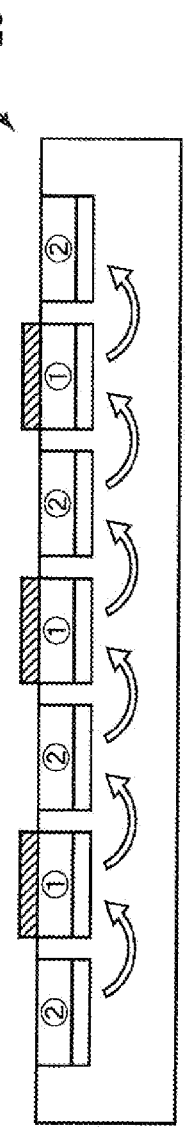
Figure 8C:
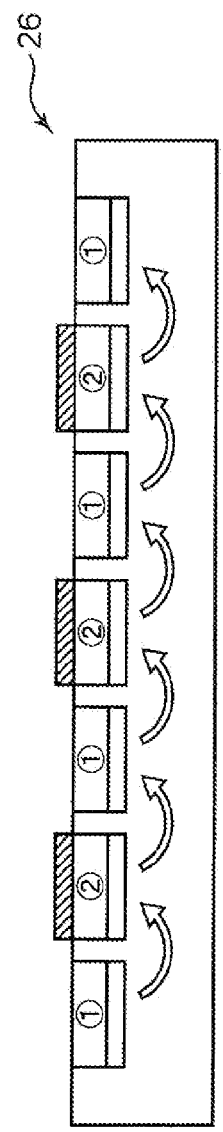

Explaining in more detail, where the image capturing unit 6 starts moving and the initial image capture signal is outputted, the first illumination unit 22a is initially lighted. As a result, the image capturing elements 42 of each odd-numbered pixel row 41 where the light-blocking filters 43 have not been formed, from among the pixel rows 41 of the light receiving unit 40A of the TDI sensor 26 are exposed, as shown in FIG. 8A, and electric charges corresponding to the received quantity of light are generated in the image capturing elements 42. The electric charges generated in the pixel rows 41 are transferred at a predetermined timing to the adjacent pixel rows 41 (even-numbered pixel rows 41). In other words, the line images created by illuminating with the first illumination unit 22a are taken in by the odd-numbered pixel rows 41, and those line images are transferred to the adjacent even-numbered pixel rows 41. Encircled numerical symbols in FIGS. 8A to 8C illustrate the relationship between the line image that is to be captured and the type of illumination. Thus, the encircled symbol 1 denotes the light image created by illuminating with the first illumination unit 22a, and the encircled symbol 2 denotes the line image created by illuminating with the second illumination unit 22b (in FIGS. 8B and 8C, the reference numerals of each unit of the TDI sensor 26 are omitted for the sake of convenience).

Where the next image capture signal is outputted following the movement of the image capturing unit 6, the second illumination unit 22b is lighted and the image capturing elements 42 of the odd-numbered pixel rows 41 are exposed, as shown in FIG. 8B, thereby generating the electric charges corresponding to the received quantity of light in the image capturing elements 42. In other words, line images created by illuminating with the second illumination unit 22b are taken in. In this case, since the even-numbered pixel rows 41 are provided with the light-blocking filters 43 and no electric charges are generated in the image capturing elements 42 of those pixel rows 41, the electric charges of the line images that have been earlier captured by illuminating with the first illumination unit 22a are held as they are, without being affected by illumination with the second illumination unit 22b. Where the exposure is completed, the electric charges of the pixel rows 41 are sequentially transferred to the adjacent pixel rows 41 at a predetermined timing.

Where the image capturing unit 6 further moves and a next image capture signal is outputted, the first illumination unit 22a is lighted and the image capturing elements 42 of the pixel rows 41 positioned in the odd rows are exposed, as shown in FIG. 8C. As a result, the newly generated electric charges are added to and accumulated with the electric charges of the line images that have been earlier captured by illuminating with the first illumination unit 22a. In this case, the electric charges are also not generated, as described above, in the image capturing elements 42 of the pixel rows 41 positioned in the even rows, and therefore the electric charges of the line images that have been earlier captured by illuminating with the second illumination unit 22b are held as they are without being affected by the illumination with the first illumination unit 22a.

Thus, the image data on the line images obtained by the addition and accumulation of electric charges of four cycles as a result of illumination with the first illumination unit 22a, those line images relating to a single image capture line of the components C (in other words, line images exposed multiple (four) times) and the image data on the line images obtained by the addition and accumulation of electric charges of four cycles as a result of illumination with the second illumination unit 22b, while alternately lighting the first lighting unit 22a and the second illumination unit 22b following the movement of the image capturing unit 6, are alternately outputted from the TDI sensor 26 over the entire length of the components C from the front end to the rear end in the relative movement direction, and those image data are sequentially outputted from the camera 21 via the image take-in device 68 to the image processing unit 65.

In the image processing unit 65, the first component image of the component C is generated from the image data group of the line images obtained by illuminating with the first illumination unit 22a, and the second component image of the components C is generated from the image data group of the line images obtained by illuminating with the second illumination unit 22b, among the image data groups of the line images inputted from the camera 21. As a result, the main control unit 61 recognizes the holding state of the components C by the mounting heads 16 on the basis of the first component image and second component image generated by the image processing unit 65.

Thus, as mentioned hereinabove, when the timing at which a site at a distance L from the distal end section of the components C (distance-L site of the component) in the direction of relative movement with respect to the image capturing unit 6 reaches a position facing the first pixel row 41 of the TDI sensor 26, with the reflecting mirror 29 being interposed therebetween, and the exposure is initially performed by lighting the illumination device 22 is taken as the first timing, and subsequent exposure timings are taken as the second timing, third timing, . . . , the sites of the components C facing the odd-numbered pixel rows 41 of the TDI sensor 26, with the reflecting mirror 29 being interposed therebetween, are captured at the same time by the exposure at each timing. In this case, the exposure is performed at the timings synchronized with the relative movement (pitch p) of the components C, while the first illumination unit 22a and the second illumination unit 22b are being switched.

More specifically, the electric charges are sequentially added up and accumulated in the odd-numbered (first, third, . . . ) pixel rows 41, following the relative movement of the components C, with respect to the distance-(L+2ap) (a=0, 1, 2, 3, . . . ) sites of the components C by lighting the first illumination unit 22a at odd-numbered timings each time the respective site faces the first pixel row 41, third pixel row 41, . . . odd-numbered pixel row 41, with the reflecting mirror 29 being interposed therebetween.

Meanwhile, the electric charges are sequentially added up and accumulated in the odd-numbered (first, third, . . . ) pixel rows 41, following the relative movement of the components C, with respect to the distance-(L+(2a+1)p) (a=0, 1, 2, 3, . . . ) sites of the components C by lighting the second illumination unit 22b at even-numbered timings each time the respective site faces the first pixel row 41, third pixel row 41, . . . odd-numbered pixel row 41, with the reflecting mirror 29 being interposed therebetween.

The accumulated electric charges for a single image capture line of the components C associated with the odd-numbered image capture timings (electric charges for the distance-(L+2ap) (a=0, 1, 2, 3 . . . ) sites obtained by lighting the first illumination unit 22a) and the accumulated electric charges for a single image capture line of the components C associated with the even-numbered image capture timings (electric charges for the distance-(L+(2a+1)p) (a=0, 1, 2, 3 . . . ) sites obtained by lighting the second illumination unit 22b) are read alternately from the pixel row 41 at one end side, in the X direction, of the TDI sensor 26 into the respective register rows 45, and the respective signals corresponding to the electric charges accumulated for a single image capture line of each site of the components C are sequentially and alternately outputted from the TDI sensor 26. Thus, the electric charges obtained by image capturing at different timings and under different illumination conditions at the odd-numbered single image capture lines and even-numbered single image capture lines with respect to the single image capture line of each pitch p (distance equal to the arrangement pitch p of the pixel rows 41) in the components C, following the movement of the image capturing unit 6, are alternately outputted from the TDI sensor 26, while being sequentially accumulated. In other words, the line images of the single image capture lines for each pitch p of the components C which are exposed multiple times at the timings and illumination conditions that differ among the adjacent single image capture lines are sequentially outputted from the TDI sensor 26 over the entire length of the components C. As a result, two component images with different illumination conditions that are constituted by a group of line images of single image capture lines for every 2 pitches (2 p) of the components C are obtained, and the main control unit 61 recognizes the holding state of the components C by the mounting heads 16 on the basis of those two component images.

As explained hereinabove, with such component mounting apparatus, it is possible to acquire the first component image obtained by illuminating with the first illumination unit 22a and the second component image obtained by illuminating with the second illumination unit 22b within a single scan of the components C, which are held by the mounting heads 16, by the image capturing unit 6.

Further, in the image capturing unit 6, the first component image and the second component image of the components C are acquired by using the camera 21 provided with the TDI sensor 26 in which the light-blocking filters 43 are formed on the even-numbered pixel rows 41, as mentioned hereinabove, as the camera for capturing the images of the components, and alternately acquiring the line images exposed multiple (four) times by illuminating with the first illumination unit 22a and the line images exposed multiple (four) times by illuminating with the second illumination unit 22b, the line images being obtained for a single image capture line of the components C. As a result, a component image with good luminosity can be acquired for either of the first component image and second component image even when the image capturing unit 6 is scanned at a comparatively high speed.

Therefore, with the component mounting apparatus, the component recognition can be performed by efficiently acquiring the first component image and the second component image, which differ from each other in illumination conditions, without increasing the component mounting apparatus in size or cost due to the installation of a high-brightness illumination device.

In particular, in the TDI sensor 26 installed at the camera 21, the light-blocking filters 43 have been formed on the even-numbered pixel rows 41 (image capturing elements 42), as described hereinabove, and such a TDI sensor 26 can be manufactured at a comparatively low cost by modifying the already existing TDI sensor, for example, by applying a coating to the image capturing elements 42 of the even-numbered pixel rows 41 and processing the image capturing elements 42 to obtain the light-blocking filters 43. Therefore, with such a component mounting apparatus, the above-described operational effect can be achieved with a comparatively inexpensive configuration.

Further, in the embodiment, an example is described in which the first component image and second component image are acquired by installing the illumination device 22 having illumination units 22a, 22b of two types at the image capturing unit 6, but it is also possible to install the illumination device 22 additionally having a third illumination unit 22c (shown in FIG. 10), and thus acquire the third component image by lighting only the third illumination unit 22c, in addition to the first and second component images.

In this case, a sensor in which two-row pixel rows 41 with the light-blocking filters 43 formed therein are arranged between the pixel rows 41 where no light-blocking filters 43 are formed, as shown in FIG. 9A, is used as the TDI sensor 26. In the example shown in the figure, the light receiving unit 40A includes 10 pixel rows 41, and the light-blocking filters 43 are formed on the pixel rows 41 other than the first, fourth, seventh, and tenth pixel rows 41, as counted from the left side in the figure.

Further, in this case, the first illumination unit 22a, second illumination unit 22b, and third illumination unit 22c are sequentially switched for each input of the image capture signal under the control by the main control unit 61 based on the timing chart shown in FIG. 10. As a result, the first to third component images constituted by image capture lines for every three pitches p of each component C are acquired in a single scan of the components C by the image capturing unit 6. The case in which the images of the components C are captured while the image capturing unit 6 moves from the (+) side to the (−) side in the X direction is explained below in greater detail.

Where the image capturing unit 6 starts moving and the initial image capture signal is outputted, the first illumination unit 22a is lighted and the image capturing elements 42 of each odd-numbered pixel row 41 where the light-blocking filters 43 have not been formed, are exposed, as shown in FIG. 9A. As a result, the line images created by illuminating with the first illumination unit 22a are taken in by the pixel rows 41, and those line images (electric charges) are transferred to the adjacent pixel rows 41 at a predetermined timing. The encircled symbol 1 in FIGS. 9A to 9D denotes the line image created by illuminating with the first illumination unit 22a, the encircled symbol 2 denotes the line image created by illuminating with the second illumination unit 22b, and the encircled symbol 3 denotes the line image created by illuminating with the third illumination unit 22c (in FIGS. 9B to 9D, the reference numerals of each unit are omitted for the sake of convenience).

Where the next image capture signal is outputted following the movement of the image capturing unit 6, the second illumination unit 22b is lighted and the image capturing elements 42 of the pixel rows 41 where no light-blocking filters 43 have been formed are exposed, as shown in FIG. 9B, whereby the line images created by illuminating with the second illumination unit 22b are taken in by the pixel rows 41. In this case, since the line images that have been earlier captured by illuminating with the first illumination unit 22a are held in the image capturing elements 42 of the pixel rows 41 where the light-blocking filters have been formed, the line images are held as they are without being affected by the illumination with the second illumination unit 22b. Where the exposure is completed, the electric charges of the pixel rows 41 are sequentially transferred to the adjacent pixel rows 41 at a predetermined timing.

Where the next image capture signal is outputted following the movement of the image capturing unit 6, the third illumination unit 22c is lighted and the image capturing elements 42 of the pixel rows 41 where no light-blocking filters 43 have been formed are exposed, as shown in FIG. 9C, whereby the line images created by illuminating with the third illumination unit 22c are taken in by the pixel rows 41. In this case, since the line images that have been earlier captured by illuminating with the first illumination unit 22a and the second illumination unit 22b are held in the image capturing elements 42 of the pixel rows 41 where the light-blocking filters have been formed, the line images are held as they are without being affected by the illumination with the third illumination unit 22c. Where the exposure is completed, the electric charges of the pixel rows 41 are sequentially transferred to the adjacent pixel rows 41 at a predetermined timing.

Where the image capturing unit 6 further moves and a next image capture signal is outputted, the first illumination unit 22a is lighted and the image capturing elements 42 of the pixel rows 41 where the light-blocking filters 43 have not been formed are exposed, as shown in FIG. 9D. As a result, the newly generated electric charges are added to and accumulated with the electric charges of the line images that have been earlier captured by illuminating with the first illumination unit 22a. In this case, the line images that have been earlier captured by illuminating with the second illumination unit 22b and the third illumination unit 22c are also held by the image capturing elements 42 of the pixel rows 41 where the light-blocking filters have been formed. Therefore, those line images are not affected by illumination with the first illumination unit 22a.

Thus, the image data on the line images obtained by the addition and accumulation of electric charges of four cycles as a result of illumination with the first illumination unit 22a, those line images relating to a single image capture line of the components C (line images exposed multiple (four) times), the image data on the line images obtained by the addition and accumulation of electric charges of four cycles as a result of illumination with the second illumination unit 22b, and the image data on the line images obtained by the addition and accumulation of electric charges of four cycles as a result of illumination with the third illumination unit 22c, while sequentially lighting the first to third lighting units 22a to 22c, following the movement of the image capturing unit 6, are sequentially outputted from the TDI sensor 26. As a result, in the image processing unit 65, the first component image is generated from the image data group of the line images created by illuminating with the first illumination unit 22a (image data group constituted by line images of each site for every three pitches (3 p) of the pixel rows 41 of the components C), from among the image data on the line images inputted from the camera 21, the second component image is generated from the image data group of the line images created by illuminating with the second illumination unit 22b (image data group of line images of each site for every three pitches (3 p) of the pixel rows 41 of the components C, this image data group being constituted by line images of each site shifted by one pitch p of the pixel rows 41 with respect to the sites of the components C which have been the image capturing objects of the first component image), and the third component image is generated from the image data group of the line images created by illuminating with the third illumination unit 22c (image data group of line images of each site for every three pitches (3 p) of the pixel rows 41 of the components C, this image data group being constituted by line images of each site shifted by two pitches 2 p of the pixel rows 41 with respect to the sites of the components C which have been the image capturing objects of the first component image).

The configuration according to the abovementioned embodiment basically may be used also in the case in which four or more illumination units are selectively lighted and four or more component images that differ from each other in illumination conditions are acquired. Essentially, it is possible to use the TDI sensor 26 equipped with the light receiving unit 40A, in which one pixel row 41 where the light-blocking filters 43 have not been formed and pixel rows 41 having the light-blocking filters 43 formed therein, the number of the latter pixel rows 41 being obtained by subtracting one from the number of the illumination units, are arranged alternately, as the TDI sensor 26 of the camera 21, and capture the images of the components C while sequentially switching the illumination units that are lighted.

Further, in the abovementioned embodiment, the case in which a plurality of component images obtained by switching the illumination units 22a, 22b, 22c of the illumination device 22, that is, a plurality of component images obtained by switching the illumination direction, is acquired is explained as an example of acquiring a plurality of component images with mutually different illumination conditions. However, for example, a plurality of component images with mutually different illumination conditions such as the illumination intensity (luminous intensity) or the color of the illumination light may be also acquired. For example, it is possible to use a device in which illumination lights of red (R), green (G), and blue (B) colors can be selectively radiated as the illumination device 22 and acquire three component images of red, green, and blue colors on the basis of the timing chart shown in FIG. 10. In this case, the color image of the components C can be generated by combining those component images in the image processing unit 65. In other words, the color image of the components C can be acquired by a single scan of the image capturing unit 6 with respect to the components C.

Second Embodiment

Figure 11:
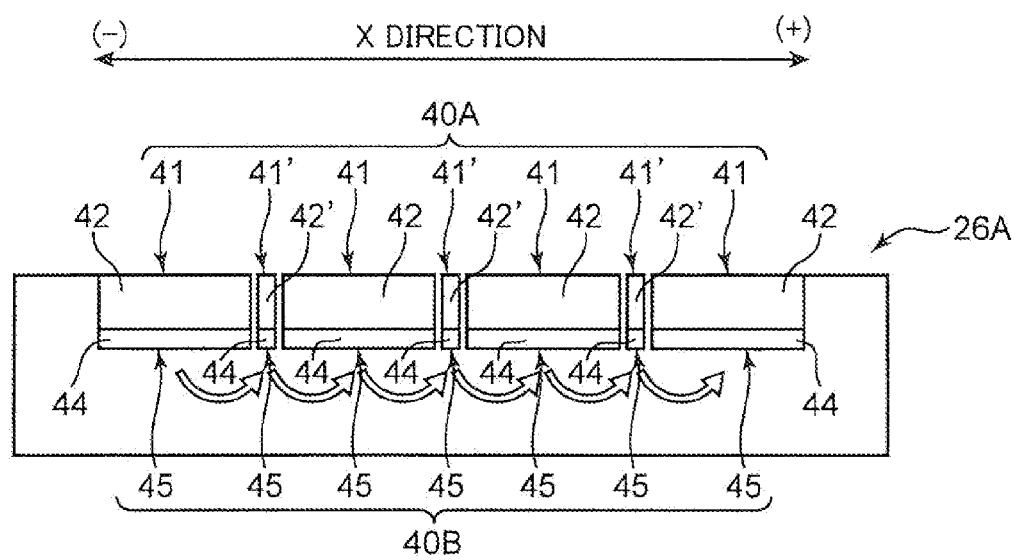
FIG. 11 illustrates schematically another configuration of the TDI sensor.

In the first embodiment, a sensor in which the light-blocking filters 43 are formed at image capturing elements 42 of specific pixel rows 41 is used as the TDI sensor 26 of the camera 21, but a TDI sensor 26A such as shown in FIG. 11 can be also used.

The TDI sensor 26A shown in the figure has a configuration in which line memory 41' is provided instead of the pixel row 41 where the light-blocking filters 43 have been formed, from among the pixel rows 41 of the TDI sensor 26 shown in FIG. 4. In the line memory 41', a plurality of capacitors 42' (correspond to charge holding units in accordance with the present disclosure) each corresponding to the respective image capturing element 42 of the pixel row 41 having the light-blocking filters 43 formed therein in the first embodiment is arranged in the direction parallel to the adjacent pixel rows 41 and has only a function of holding the electric charges transferred from the image capturing elements 42 of the adjacent pixel rows 41. In the TDI sensor 26A, the register rows 45 read the electric charges from the image capturing elements 42 of the corresponding pixel rows 41 or the capacitors 42' of the line memories 41', and the read-out charges are transferred to the image capturing elements 42 of the adjacent pixel rows 41 or the capacitors 42' of the line memories 41', as shown by the outline arrows in the figure.

With such a TDI sensor 26A, the degree of freedom in selecting the shape is high to the extent that no light reception area should be ensured for the line memories 41', by contrast with the pixel rows 41. For this reason, as shown in the figure, the line memories 41' can be formed narrower in the X direction (arrangement direction of the pixel rows 41) than the pixel rows 41. With such a TDI sensor 26A, the number of pixel rows 41 (effective pixel rows 41 that can be exposed) that can be arranged in the same range as that of the TDI sensor 26 shown in FIG. 4 can be larger than that in the TDI sensor 26. As a result, when alternate image capturing is performed under two illumination conditions, the width ratio of the line images of the sites of the components C can be made larger than the width ratio of the lines for which no image is captured (therefore, the line images of the cites of the components C obtained under the two illumination conditions partially overlap), and a resolution (resolution in the X direction) that can be realized with respect to the two component images obtained under the two illumination conditions can be higher than that of the TDI sensor 26 shown in FIG. 4. Therefore, the merit of using the camera 21 equipped with the TDI sensor 26A is that two component images of higher accuracy can be acquired by using the configuration substantially identical to that of the first embodiment. Conversely, where the resolution (resolution in the X direction) is the same as that of the TDI sensor 26 shown in FIG. 4, the TDI sensor 26A can be reduced in size in the X direction with respect to the TDI sensor 26. The resultant merit in this case is that the camera 21 can be miniaturized, thereby contributing to the reduction in size and weight of the image capturing unit 6.

As mentioned hereinabove, when the width size (size in the X direction) of the memories 41' is less than the width size of the pixel rows 41, as mentioned hereinabove, the pitches of the pixel rows 41 and the rows including the line memories 41' differ from each other. Therefore, when the camera 21 equipped with the TDI sensor 26A is used, the image capture signals may be outputted from the main control unit 61 to the camera 21 according to the output signals from the linear encoder 36 so that the switching of the illumination device 22, the exposure with image capturing elements 42 of the pixel rows 41 (operation of taking in the line images), and the transfer of electric charges (line images) may be adequately performed on the basis of the pitches.

A TDI sensor equipped with the line memories 41' instead of the pixel rows 41 where the light-blocking filters 43 have been formed, from among the pixel rows 41 of the TDI sensor 26, for example, shown in FIGS. 9A to 9D, can be used as a TDI sensor similar to the TDI sensor 26A. With the configuration of such a TDI sensor, it is possible to acquire the component images with a resolution (resolution in the X direction) higher than that of the TDI sensor 26A, while acquiring three component images under illumination conditions of three types in the same manner as with the TDI sensor 26 shown in FIG. 9.

Third Embodiment

Figure 12:
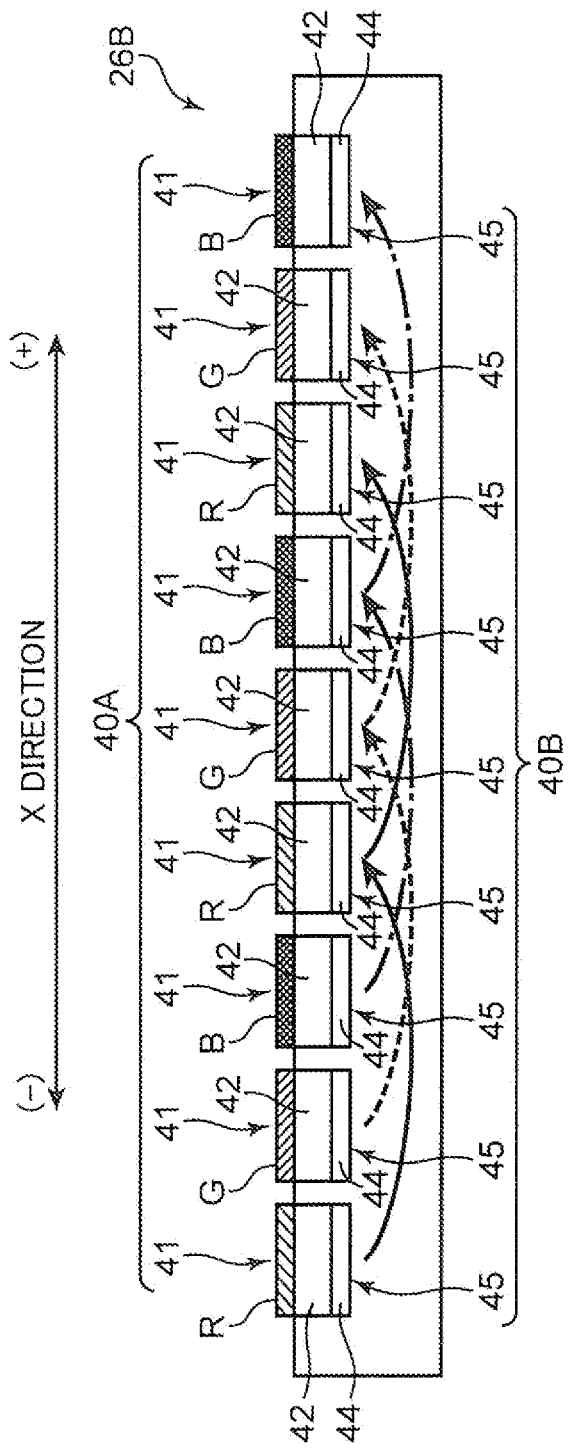
FIG. 12 illustrates schematically another configuration of the TDI sensor.

The camera 21 equipped with a TDI sensor 26B such as shown in FIG. 12 can be also used as the camera 21 of the image capturing unit 6.

The TDI sensor 26B shown in the figure has a configuration in which a pixel row group constituted by a plurality of pixel rows 41 that is arranged continuously in a predetermined sequence and has mutually different wavelengths of light that can be received is taken as a unit, and a plurality of such pixel row groups is arranged in a row. More specifically, the sensor has a configuration in which a group including a pixel row 41 that is equipped with a red filter R and, therefore, can receive only red light, a pixel row 41 that is equipped with a green filter G and, therefore, can receive only green light, and a pixel row 41 that is equipped with a blue filter B and, therefore, can receive only blue light, and having those pixel rows arranged in a predetermined sequence is taken as one pixel row group, and a plurality (three in the example shown in the figure) of such pixel row groups is arranged in a row.

When the camera 21 equipped with the TDI sensor 26B is used, the main control unit 61 controls the illumination control unit 66 that should light only the predetermined illumination unit from among the first illumination unit 22a and the second illumination unit 22b according to the components C. Further, the main control unit 61 moves the image capturing unit 6 at a constant speed (moves relative to the components C), and the image capture signals are outputted at the timings the image capturing unit 6 moves through a distance which is three times the arrangement pitch of the pixel rows 41. Thus, the illumination units are lighted at the abovementioned timings by controlling the illumination control unit 66. The main control unit 61 then controls the camera control unit 50 to expose the image capturing elements 42 of the pixel rows 41 of the TDI sensor 26 according to the input of the image capture signals from the main control unit 61, and controls the clock driver 54 so that the transfer of the line images (electric charges) is performed three times per such one-cycle exposure. In other words, as shown by the solid lines, broken lines, and dot-dash lines in the figure, the electric charge transfer timing is controlled such that the electric charges of the pixel rows 41 belonging to each pixel row group are transferred to the pixel rows 41 corresponding to the adjacent pixel row group, that is, to the pixel rows 41 having the same filter formed therein.

In the component mounting apparatus using the camera 21 equipped with such a TDI sensor 26B, the component images of red, green, and blue colors are acquired as the images of the components C within one scan of the image capturing unit 6 with respect to the components C. Thus, where the movement of the image capturing unit 6 is started and the initial image capture signal is outputted from the main control unit 61, the image capturing elements 42 of the pixel rows 41 are exposed, whereby the red, green, and blue line images are taken in by the pixel rows 41 of the pixel row groups. Those line images are transferred to the corresponding pixel rows 41 of the adjacent pixel row groups. Therefore, as a result of the line images being sequentially transferred to the corresponding pixel rows 41 of the adjacent pixel row groups, while the pixel rows 41 are being exposed, the red, green and blue line images which are the line images of the same image capture line and are obtained by respective multiple exposures are outputted from the TDI sensor 26B to the image processing unit 65.

The image processing unit 65 generates an image on the basis of the line images with a common light reception wavelength, that is, the line images of the same color, from among the line images outputted from the TDI sensor 26B, whereby a component image constituted by a line image group of the sites of the components C for every three pitches of the pixel rows 41 is generated for each of the three colors, and the color image of the components C is generated by combining those images. Therefore, the main control unit 61 recognizes the holding state of the components C by the mounting heads 16 on the basis of the color image of the components C.

In the case explained herein, the color image of the components C is generated by acquiring the component images of three primary colors, but the abovementioned configuration also makes it possible to acquire, for example, an IR (infrared) image and an image with blocked IR radiation as the images of the components C. In such a case, a sensor in which a pixel row 41 receiving only IR radiation as a result of providing IR-transmitting filters and a pixel row 41 receiving light other than IR radiation as a result of providing IR-blocking filters are taken as a single pixel row group, and a plurality of such pixel row groups is arranged in a row may be used as the TDI sensor 26B.

Other Embodiments (1) In the above-described embodiments, the configuration is explained in which the image capturing unit 6 is installed on the head unit 5 and the image capturing unit 6 is moved with respect to the components C attached to and held by the mounting heads 16, but such a configuration is not limiting. For example, a configuration may be also used in which the image capturing unit is fixedly disposed at the base 1, and the image of the components C held by the mounting heads 16 is captured by moving the head unit 5 relative to the image capturing unit under the control by the main control unit 61. In this case, the camera may be disposed to face upward, and the reflective light (component image) from the components C may be taken in directly by the camera 21 under the illumination with the illumination device 22, without introducing the reflecting mirror.

In this case, the head unit drive mechanism that moves the head unit 5 in the XY direction and the control device 60 are the moving device in accordance with the present disclosure.

(2) In the abovementioned embodiments, the head unit 5 has a plurality of mounting heads 16 arranged in a row in the X direction, but the plurality of mounting heads 16 may be arranged in two, front and rear, rows (two rows in the Y direction). In this case, the number of pixels in the pixel rows 41 of the TDI sensor 26 may be set such that the images of the components C held by the front and rear mounting heads 16 could be captured simultaneously by the TDI sensor 26. Further, for example, when the illumination conditions of the components C attached to the front and rear mounting heads 16 differ from each other, it is possible to acquire the component images with mutually different illumination conditions including the front and rear components C, while alternately switching the illumination conditions, extract the component images captured under the illumination conditions corresponding to the components C on one side, from among the front and rear components C, from those component images in the image processing unit 65, generate the component image of the components C on the one side by the extracted component images, and similarly generate the component images with respect to the components C on the other side.

(3) In the first embodiment (example shown in FIG. 8), an example is explained in which component images of two types are acquired with the TDI sensor 26 by alternately lighting the first illumination unit 22*a* and the second illumination unit 22*b*, but a configuration may be also used in which the image capturing mode in which component images of two types are acquired by alternately switching the two illumination units 22*a*, 22*b* according, for example, to the type of the components C and the image capturing mode in which a component image of one type is acquired by lighting either of the first illumination unit 22*a* and the second illumination unit 22*b* are switched by the control device 60. A similar configuration may be also used in the example shown in FIG. 9. Further, in the example shown in FIG. 9, the component images of two types can be acquired by performing the initial two exposures, from among the three (first to third timings) consecutive exposures, by lighting a common illumination unit (for example, the first illumination unit 22*a*) and performing the last exposure by lighting a different illumination unit (for example, the second illumination unit 22*b*). Therefore, in the example shown in FIG. 9, the image capturing modes in which the component image of one type, component images of two types, and component images of three types are acquired may be switched by the control device 60 according to the type of the components C.

(4) In the abovementioned embodiments, the configuration is explained in which the image capturing apparatus in accordance with the present disclosure is installed on the surface mounting machine, but such a configuration is not limiting. For example, the image capturing apparatus can be installed on a component testing apparatus for inspecting electronic components such as IC chips.

Figure 13:
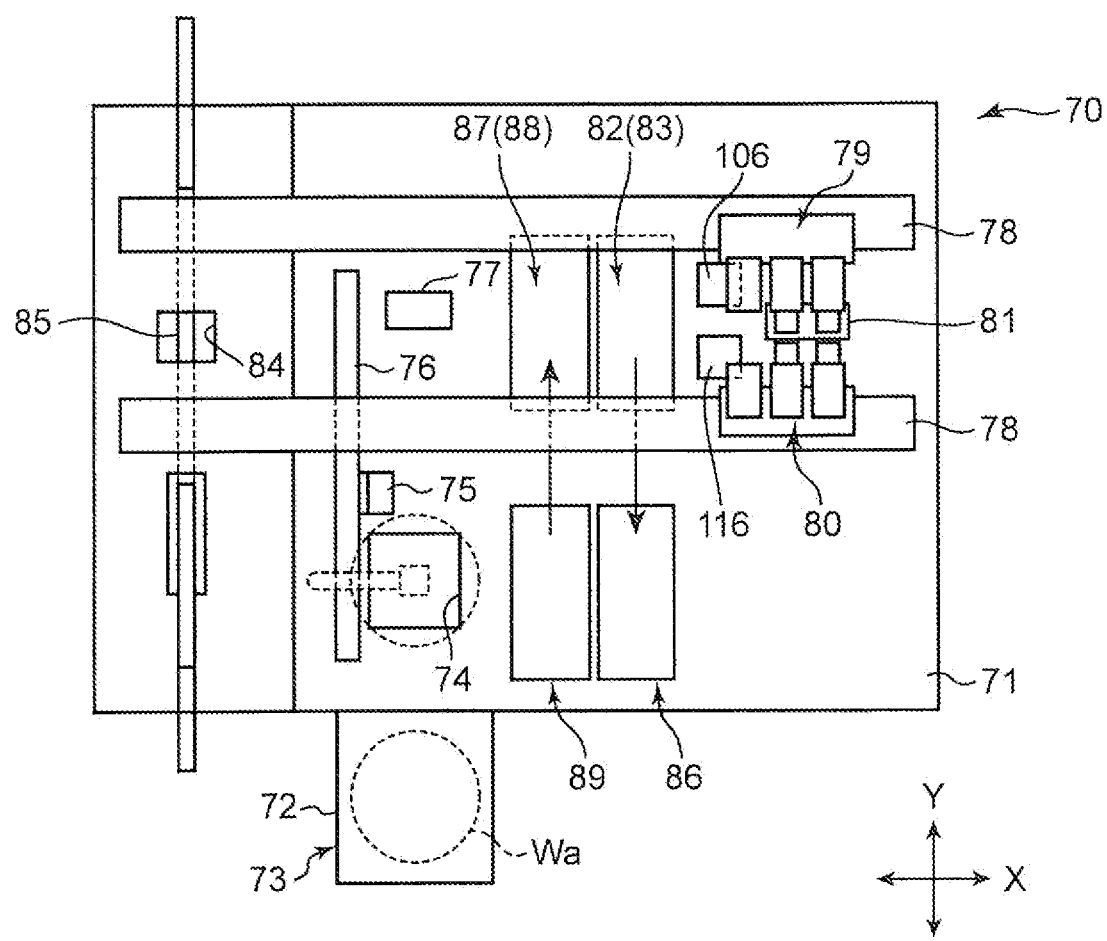
FIG. 13 is a plan view illustrating schematically the component testing apparatus using the image capturing apparatusin accordance with the present disclosure.

FIG. 13 is a plan view illustrating a component testing apparatus 70 (corresponding to the component testing apparatus in accordance with the present disclosure) having installed thereon the image capturing apparatus in accordance with the present disclosure. In the figure, the XY coordinate axes are shown to clarify the dimensional relationship.

As shown in the figure, the cassette placing unit 73 capable of loading a cassette 72 in which wafers Wa with diced bare chips are accommodated in multiple stages in the vertical direction is provided on a base 71 of a component testing apparatus 70. The cassette 72 loaded on the cassette placing unit 73 is conveyed by a conveying mechanism (not shown in the figure) to a position below an opening 74 formed in the base 71, and the bare chips are lifted at this position with a take-out member 75. The take-out member 75 conveys the bare chips from the opening 74 to a component standby unit 77 along a rail 76 extending in the Y direction on the base 71. The component standby unit 77 is disposed between a pair of rails 78 extending in the X direction on the base 71. The bare chips carried to the component standby unit 77 are conveyed to an inspection socket 81 on the base 71 by a pair of head units 79, 80 driven along the rails 78, and the bare chips are subjected to the predetermined inspection. The head units 79, 80 have a head for chip attachment, and the bare chips are attached and held by the head.

In such a component testing apparatus 70, image capturing units 106, 116 are fixedly provided between the component standby unit 77 and the inspection socket 81 (corresponding to the inspection unit in accordance with the present disclosure) on the base 71. The image capturing units 106, 116 include a camera for capturing, from below, the images of the bare chips held by the head units 79, 80, an illumination device, and a casing integrally holding the camera and the illumination device (details of this configuration are herein omitted). For example, a camera equipped with a TDI sensor similar to the TDI sensor shown in FIG. 4 is provided as the camera, and an illumination device having a plurality of illumination units that have mutually different illumination directions is provided similarly to the illumination device 22 shown in FIG. 3.

The image capturing units 106, 116 capture the images of the bare chips conveyed from the component standby unit 77 to the inspection socket 81, and a control device (not shown in the figure) detects defects (for example, a bump height defects) on the basis of the image data. In this case, the conveyance speed of the bare chips, the timings of image capturing with the camera (TDI sensor), the switching timing of the illumination units, and the transfer timing of line images (electric charges) in the TDI sensor are controlled by the control device (not shown in the figure) as in the above-described component mounting apparatus. As a result, a plurality of images with different illumination conditions are acquired as the bare chip is conveyed in one direction above the image capturing units 106, 116, and the control unit determines the presence of defects in the bare chips on the basis of this plurality of images.

The bare chips detected to be defective are conveyed by the head units 79, 80 to a defective product tray 83 placed on a defective product recovery unit 82 on the base 71. In addition, the control device detects the posture of the base chips with respect to the head units 79, 80 on the basis of the plurality of images. In this case, the bare chips detected to be displaced with respect to the head units 79, 80 are conveyed to the inspection socket 81 after the position thereof is corrected by the head units 79, 80.

The bare chips determined to be defective by the inspection in the inspection socket 81 are conveyed by the head units 79, 80 to the defective product tray 83, but the bare chips that are detected to be free of defects are conveyed by the head units 79, 80 to the component accommodation unit 84 on the base 71 and accommodated in a base tape 85 for a tape feeder in the component accommodation unit 84, and a cover tape (not shown in the figure) is pasted therein in the base tape 85.

Where the defective product tray 83 of the defective product recovery unit 82 is full, the tray 83 is transferred by a tray movement mechanism (not shown in the figure) to a tray discharge unit 86. The tray 88 located in the tray standby unit 87 adjacent to the defective product recovery unit 82 is transferred by the head units 79, 80 to the defective product recovery unit 82, and an empty tray is transferred by a tray movement mechanism (not shown in the figure) from an empty tray placement unit 89 to the tray standby unit 87.

In this embodiment, the image capturing units 106, 116, head units 79, 80, drive mechanism for the head units, control device and the like correspond to the image capturing apparatus in accordance with the present disclosure. Among them, the head units 79, 80 and the drive mechanism for the head units correspond to the moving device of the image capturing apparatus, and the control device corresponds to the image capture control device in accordance with the present disclosure. Further, the head unit drive mechanism and control device correspond to the forwarding device in accordance with the present disclosure.

In the configuration explained herein, the image capturing units 106, 116 are disposed on the base 71 of the component testing apparatus 70, but such configuration is not limiting, and for example the configuration can be also used in which the image capturing units 106, 116 are movably attached to the head units 79, 80, in the same manner as in the component mounting apparatus shown in FIG. 2 or the like.

(5) The image capturing apparatus in accordance with the present disclosure can be installed not only on the component mounting apparatus or component testing apparatus, as described hereinabove, but also on a printed substrate inspection apparatus (one of the substrate inspection apparatuses in accordance with the present disclosure) that inspects a substrate printed with a paste such as a soldering paste in a screen printing apparatus. The printed substrate inspection apparatus includes a substrate holding unit that holds the substrate substantially horizontally, an image capturing unit that is supported to be capable of moving in a plane (XY directions) parallel to the printed substrate relative to the printed substrate held by the substrate holding unit, a drive mechanism (corresponds to the moving device in accordance with the present disclosure) that moves the image capturing unit and the substrate relative to each other, and a control device for integrally controlling the aforementioned units. The image capturing unit includes a camera for capturing the image of the substrate from above, an illumination device, and a casing in which the camera and the illumination device are integrally held. A camera equipped with a TDI sensor equivalent to the TDI sensor shown in FIG. 4 is provided as the camera, and the illumination device has a plurality of illumination units with mutually different illumination directions, similarly to the illumination device 22 shown in FIG. 3.

Thus, the printed substrate inspection apparatus detects the defective places on the basis of the image data by capturing the images of printed places, while moving the image capturing unit with respect to the substrate. In this case, the conveyance speed of the image capturing unit, the timings of image capturing with the camera (TDI sensor), the switching timings of the illumination units, the transfer timings of line images (electric charges) in the TDI sensor and the like are controlled by the control device (not shown in the figure) as in the above-described component mounting apparatus. As a result, a plurality of images with different illumination conditions are acquired as the image capturing unit is moved in one direction above the printed places, and the control device determines whether or not the printed places are defective on the basis of this plurality of images.

(6) The image capturing apparatus in accordance with the present disclosure can be also installed at a mounted substrate inspection apparatus (one of the substrate inspection apparatuses in accordance with the present disclosure). The mounted substrate inspection apparatus captures the images of component mounted places on a substrate with a camera and recognizes the mounting state of the components on the basis of the image data. The configuration equivalent to that of the above-described printed substrate inspection apparatus can be used for the mounted substrate inspection apparatus. With the mounted substrate inspection apparatus, it is possible to acquire a plurality of images with different illumination conditions and determine whether or not the component mounting is defective on the basis of this plurality of images, in the same manner as in the printed substrate inspection apparatus.

The specific configurations of the TDI sensor, image capturing apparatus, component mounting apparatus, component testing apparatus, printed substrate inspection apparatus, and mounted substrate inspection apparatus, which are described by way of examples in the embodiments of the present disclosure, can be changed, as appropriate, without departing from the essence of the present disclosure. Further, although not described specifically, the configuration, for example, of the image capturing unit that is explained in the component mounting apparatus can be likewise applied to a component testing apparatus and a substrate inspection apparatus such as a printed substrate inspection apparatus and mounted substrate inspection apparatus (such applications are, however, not described herein).

The above-described present disclosure is summarized below.

Thus, the TDI sensor according to one aspect of the present disclosure is a TDI sensor that performs an operation of capturing a line image at predetermined timings and outputs, as an image of each image capture line, the line image exposed a plurality of times. The TDI sensor including: a light receiving unit including pixel rows each having a plurality of image capturing elements arranged in a first direction and generating and holding electric charges corresponding to respective exposure amounts, and electric charge holding rows each having a plurality of electric charge holding sections having only a function of holding the electric charges and arranged in the first direction so as to correspond to respective image capturing elements of the pixel rows. One of the pixel rows and one or a plurality of the electric charge holding rows being alternately arranged in a second direction orthogonal to the first direction. A transfer unit sequentially, on a row-by-row basis, transfers electric charges held by the image capturing elements of the pixel rows and the electric charge holding sections of the electric charge holding rows to adjacent rows, and outputs, as a signal of the line image, a signal corresponding to electric charges finally accumulated by the transfer.

An image capturing apparatus according to another aspect of the present disclosure is an image capturing apparatus for capturing images of an object under a specific number and a plurality of illumination conditions. The image capturing apparatus including: a TDI sensor which is the abovementioned TDI sensor having, as the light receiving unit, a light receiving unit in which one of the pixel rows and the electric charge holding rows, the number thereof being obtained by subtracting one from the specific number, are arranged alternately; a moving device for moving the object in the second direction relative to the TDI sensor; an illumination device capable of illuminating the object moved by the moving device and changing the illumination condition thereof to the plurality of illumination conditions; an image capture control device for controlling an image capture timing of the TDI sensor and a switching timing of the illumination conditions of the illumination means so that the line images of the object for each of the illumination conditions are taken in by the image capturing elements of the pixel rows, while the illumination condition of the illumination device is sequentially switched to the plurality of illumination conditions as the object is moved relative to the TDI sensor, and also for controlling transfer timings of the electric charges in the TDI sensor so that the electric charges are transferred synchronously with the image capture timing; and an image processing device for generating the specific number of images of the object by generating images of the object on the basis of line images with mutually common illumination conditions, from among the line images outputted from the TDI sensor.

In the image capturing apparatus, for example, when the images under two illumination conditions (first illumination condition and second illumination condition) are acquired, a sensor in which pixel rows and electric charge holding rows are arranged alternately is provided as the TDI sensor, and a device that can be changed to two illumination conditions is provided as the image capturing device.

With such an image capturing apparatus, as a result of performing the image capturing operation while switching the illumination conditions during the relative movement of the object, it is possible to acquire two images with different illumination conditions as the images of the object as the object moves relative to the TDI sensor. More specifically, the image capturing elements of each pixel row are initially exposed under the first illumination condition, following the movement of the object, whereby a line image (referred to as first illumination image) is taken in by the pixel rows. The line images (that is, electric charges) of the pixel rows are transferred to and held by the adjacent charge holding rows before the next exposure is performed. The image capturing elements of the pixel rows are then exposed under the second illumination condition, whereby the line images (referred to as second illumination image) is taken in by the pixel rows. In this case, the first illumination image is held in the electric charge holding units and is, therefore, not affected by the illumination light. The second illumination image of the pixel rows is thereafter transferred to the adjacent electric charge holding sections, and the first illumination image of the electric charge holdings sections is transferred to the adjacent pixel rows. Then, the image capturing elements of the pixel rows are exposed under the first illumination condition, thereby re-exposing the first illumination image in the pixel rows (electric charges are added up). Thus, a line image exposed a plurality of times under the first illumination condition, which is the line image of a specific single image capture line of the object, and a line image exposed a plurality of times under the second illumination condition, which is the line image of the following single image capture line of the object, are outputted alternately from the TDI sensor. The component image under the first illumination condition and the component image under the second illumination condition are then generated by generating the image of the object on the basis of line images with common illumination conditions, from among the light images outputted from the TDI sensor, in the image processing device.

In the TDI sensor, the electric charge holding rows may hold the line images (electric charges) in a state that is unaffected by the illumination light. Therefore, the electric charge holding rows may have capacitors arranged as the electric charge holding sections and also may be pixel rows which are equivalent to the aforementioned pixel rows, but in which a light-blocking section preventing the incidence of light is formed on the surface of each image capturing element. Where the former configuration is used in this case, the TDI sensor can be manufactured comparative easily and inexpensively by the conventional semiconductor process. In addition, the degree of freedom in selecting the shape of the electric charge holding sections is high. Therefore, for example, where the electric charge holding row is made to have a width less than a width of the pixel row in the second direction, the TDI sensor can be reduced in size in the second direction, while maintaining the resolution in the same direction. Meanwhile, where the latter configuration is used, the TDI sensor can be easily obtained, for example, by additionally providing light-blocking sections on the specific pixel rows of the already existing TDI sensor.

Further, in the image capturing apparatus, the illumination device may be configured to be capable of irradiating selectively the object with illumination lights of three primary colors, as the illumination conditions, and the image processing device may generate images of the three primary colors as the plurality of images of the object, and generate a color image by combining the images of the three primary colors.

With such a configuration, the color image of the object can be acquired by moving the component only once relative to the TDI sensor.

The TDI sensor according to another aspect of the present disclosure is a TDI sensor that performs an operation of capturing a line image at predetermined timings and outputs, as an image of each image capture line, the line image exposed a plurality of times. The sensor including: a light receiving unit including a plurality of pixel rows each having a plurality of image capturing elements arranged in a first direction and generating and holding electric charges corresponding to respective exposure amounts, those pixel rows being arranged in a second direction orthogonal to the first direction; and a transfer unit that sequentially, on a row-by-row basis, transfers electric charges held by the pixel rows to adjacent rows and outputs, as a signal of the line image, a signal corresponding to electric charges finally accumulated by the transfer, wherein the light receiving unit has a configuration in which a pixel row group constituted by a plurality of pixel rows arranged continuously in a predetermined sequence in the second direction and having mutually different wavelengths of light that can be received is taken as a unit, and a plurality of such pixel row groups is arranged in the second direction.

The image capturing apparatus according to another aspect of the present disclosure is an image capturing apparatus for capturing images of an object and acquiring images of a plurality of types. The image capturing apparatus including: the TDI sensor; a moving device for moving the object in the second direction relative to the TDI sensor; an illumination device for illuminating the object moved by the moving device; an image capture control device for controlling an image capture timing of the TDI sensor so that the line images of the object are taken in by the image capturing elements of the pixel rows, as the object is moved relative to the TDI sensor, and also for controlling transfer timings of the electric charges so that the electric charges of each pixel row belonging to each pixel row group are transferred to the pixel row corresponding to the adjacent pixel row group after the image capture operation of the TDI sensor and before the next image capture operation; and an image processing device for generating images of the object, the number thereof corresponding to the number of the pixel rows included in the pixel row group, by generating images of the object on the basis of line images with a common light reception wavelength, from among the line images outputted from the TDI sensor.

In such an image capturing apparatus, a plurality of images with mutually different wavelengths of the received light is acquired as images of the object, as the object moves relative to the TDI sensor. Thus, the line images with mutually different wavelengths are taken in by respective pixel rows by exposing the image capturing elements of the pixel rows included in the pixel row group, following the movement of the object. Those line images (charges) of the pixel rows are transferred to and held in the corresponding pixel rows of the adjacent pixel row group before the next exposure. Thus, line images exposed a plurality of times, which are a plurality of line images with mutually different wavelengths of the received light, are sequentially outputted from the TDI sensor. Further, in the image processing device, the images of the object are generated on the basis of line images with a common light reception wavelength, from among the line images outputted from the TDI sensor, whereby the images of the object, the number thereof corresponding to the number of the pixel rows included in the pixel row group, are generated.

In the image capturing apparatus, the TDI sensor has, as the pixel row group, a pixel row group including three pixel rows, each capable of receiving only light of a respective one of three primary colors; and the image processing device generates an image of the object of the respective one of three primary colors on the basis of line images with a common color, from among the line images outputted from the TDI sensor, and generates a color image of the object by combining the images of the three primary colors.

With such a configuration, the color image of the object can be acquired by moving the component only once relative to the TDI sensor.

A component mounting apparatus according to another aspect of the present disclosure includes: a head capable of holding a component; the abovementioned image capturing apparatus for capturing an image of the component as an object; and a forwarding device for forwarding the component with the head onto a substrate upon recognizing a holding state of the component using the head on the basis of image data on the component which is held by the head and the image of which has been captured by the image capturing apparatus, wherein the moving device of the image capturing apparatus moves the head and the TDI sensor relative to each other in the second direction, and the forwarding device mounts the component on the substrate by moving the head relative to the substrate.

With the component mounting apparatus, a plurality of component images is acquired as component images of the component by moving the component, which is held by the head, only once with respect to the TDI sensor. Further, the component is mounted on the substrate upon recognizing the holding state of the component with the head on the basis of the component images.

A component testing apparatus according to another aspect of the present disclosure includes: a head capable of holding a component; the abovementioned image capturing apparatus for capturing an image of the component as an object; and a forwarding device for forwarding the component with the head onto a predetermined inspection unit upon recognizing a holding state of the component with the head on the basis of image data on the component which is held by the head and the image of which has been captured by the image capturing apparatus, wherein the moving device of the image capturing apparatus moves the head and the TDI sensor relative to each other in the second direction, and the forwarding device places the component on the inspection unit by moving the head relative to the inspection unit.

With the component testing apparatus, a plurality of component images is acquired as component images of the component by moving the component, which is held by the head, only once with respect to the TDI sensor. Further, the component is mounted on the substrate upon recognizing the holding state of the component with the head on the basis of the component images.

A substrate inspection apparatus according to another aspect of the present disclosure includes: the abovementioned image capturing apparatus for capturing an image of a substrate, as an object, subjected to printing or having a component mounted thereon; and recognition device for recognizing a printing state or a component mounting state on the basis of an image of an inspection object location which is captured by the image capturing apparatus, wherein the moving device of the image capturing apparatus moves the substrate and the TDI sensor relative to each other in the second direction.

With the substrate testing apparatus, a plurality of images is acquired as component images of the inspection object location on the substrate by moving the substrate only once with respect to the TDI sensor, and the printing state or component mounting state is recognized on the basis of a plurality of images.

INDUSTRIAL APPLICABILITY

As described hereinabove, the TDI sensor, image capturing apparatus, component mounting apparatus, component testing apparatus, and substrate inspection apparatus in accordance with the present disclosure are capable of effectively and rapidly acquiring component images of a plurality of types and are useful in the field of manufacturing component-mounted substrates.

The invention claimed is:

1. An image capturing apparatus for capturing images of a first component and a second component under mutually different illumination conditions, the image capturing apparatus comprising:
   a TDI sensor having: a light receiving unit including pixel rows each having a plurality of image capturing elements arranged in a first direction and generating and holding electric charges corresponding to respective exposure amounts, and electric charge holding rows each having a plurality of electric charge holding sections having only a function of holding the electric charges and being arranged in the first direction so as to correspond to respective image capturing elements of the pixel rows, one of the pixel rows and one or a plurality of the electric charge holding rows being alternately arranged in a second direction orthogonal to the first direction; and a transfer unit sequentially, on a row-by-row basis, transferring electric charges held by the image capturing elements of the pixel rows and the electric charge holding sections of the electric charge holding rows to adjacent rows, and the transfer unit outputs, as a signal of a line image, a signal corresponding to electric charges finally accumulated by the transfer;
   a moving device including two heads arranged in the first direction for moving the first component and the second component at the same time in the second direction relative to the TDI sensor in a state in which the two components are respectively held by the two heads;
   an illumination device capable of illuminating the two components moved by the moving device at the same time under the same illumination conditions, and changing an illumination condition thereof to illumination conditions of the two components;
   an image capture control device for controlling an image capture timing of the TDI sensor and a switching timing of the illumination conditions of the illumination device so that line images of the two components for each of the illumination conditions are taken in at the same time by the image capturing elements of the pixel rows, while the illumination condition of the illumination device is sequentially switched to the illumination conditions of the two components as the two components are moved relative to the TDI sensor, and also for controlling transfer timings of the electric charges in the TDI sensor so that the electric charges are transferred synchronously with the image capture timing; and
   an image processing device for generating images of the first component by extracting images of the first component from the line images of the two components captured under the illumination condition of the first component, and generating images of the second component by extracting images of the second component from the line images of the two components captured under the illumination condition of the second component, from among the line images outputted from the TDI sensor.

2. The image capturing apparatus according to claim 1, wherein
the electric charge holding row is a pixel row which is equivalent to the pixel row, and includes a light-blocking section preventing incidence of light on a surface of each image capturing element.

3. The image capturing apparatus according to claim 1, further comprising
a forwarding device for forwarding the component with the head onto a substrate upon recognizing a holding state of the component using the head on the basis of image data on the component, wherein
the forwarding device mounts the component on the substrate by moving the head relative to the substrate.

4. The image capturing apparatus according to claim 1, further comprising
a forwarding device for forwarding the component with the head onto a predetermined inspection unit upon recognizing a holding state of the component with the head on the basis of image data on the component, wherein
the forwarding device places the component on the inspection unit by moving the head relative to the inspection unit.

5. An image capturing apparatus for capturing images of a component under a specific number and a plurality of illumination conditions, the image capturing apparatus comprising:
a TDI sensor having: a light receiving unit including pixel rows each having a plurality of image capturing elements arranged in a first direction and generating and holding electric charges corresponding to respective exposure amounts, and electric charge holding rows each having a plurality of electric charge holding sections having only a function of holding the electric charges and being arranged in the first direction so as to correspond to respective image capturing elements of the pixel rows, one of the pixel rows and one or a plurality of the electric charge holding rows, a number thereof being obtained by subtracting one from the specific number, being alternately arranged in a second direction orthogonal to the first direction; and a transfer unit sequentially, on a row-by-row basis, transferring electric charges held by the image capturing elements of the pixel rows and the electric charge holding sections of the electric charge holding rows to adjacent rows, and the transfer unit outputs, as a signal of a line image, a signal corresponding to electric charges finally accumulated by the transfer;
a moving device having a head capable of holding a component for moving the component in the second direction relative to the TDI sensor in a state in which the component is held by the head;
an illumination device capable of illuminating the component moved by the moving device and changing the illumination conditions thereof to the plurality of illumination conditions;
an image capture control device for switching, according to a type of the component held by the head, a first image capture mode in which line images of the component for each of the illumination conditions are taken in by the image capturing elements of the pixel rows, while the illumination condition of the illumination device is sequentially switched to the plurality of illumination conditions as the component is moved relative to the TDI sensor, and a second image capture mode in which line images of the component are taken in by the image capturing elements of the pixel rows in a state in which the illumination condition of the illumination device is fixed to a single illumination condition, from among the plurality of illumination conditions, by controlling the TDI sensor and the illumination device; and
an image processing device for generating the specific number of component images of a plurality of types by generating images of the component on a basis of line images with mutually common illumination conditions, from among the line images outputted from the TDI sensor in the first image capture mode, and generating an image of a component of one type on a basis of the line images outputted from the TDI sensor in the second image capture mode.

6. The image capturing apparatus according to claim 1, wherein
the electric charge holding row includes capacitors arranged as the electric charge holding sections.

7. The image capturing apparatus sensor according to claim 6, wherein
the electric charge holding row has a width less than a width of the pixel row in the second direction.

8. The image capturing apparatus according to claim 5, wherein
the electric charge holding row includes capacitors arranged as the electric charge holding sections.

9. The image capturing apparatus sensor according to claim 8, wherein
the electric charge holding row has a width less than a width of the pixel row in the second direction.

10. The image capturing apparatus according to claim 5, wherein
the electric charge holding row is a pixel row which is equivalent to the pixel row, but in which a light-blocking section preventing incidence of light is formed on a surface of each image capturing element.

11. The image capturing apparatus according to claim 5, further comprising
a forwarding device for forwarding the component with the head onto a substrate upon recognizing a holding state of the component using the head on the basis of image data on the component, wherein
the forwarding device mounts the component on the substrate by moving the head relative to the substrate.

12. The image capturing apparatus according to claim 5, further comprising
a forwarding device for forwarding the component with the head onto a predetermined inspection unit upon recognizing a holding state of the component with the head on the basis of image data on the component, wherein
the forwarding device places the component on the inspection unit by moving the head relative to the inspection unit.

* * * * *